US006995835B2

(12) United States Patent
Samsoondar et al.

(10) Patent No.: US 6,995,835 B2
(45) Date of Patent: Feb. 7, 2006

(54) METHOD AND APPARATUS FOR MEASURING ANALYTES IN BLOOD BAGS

(75) Inventors: James Samsoondar, Cambridge (CA); Duncan MacIntyre, Campbellville (CA)

(73) Assignee: NIR Diagnostics Inc., (CA)

( * ) Notice: Subject to any disclaimer, the term of this patent is extended or adjusted under 35 U.S.C. 154(b) by 546 days.

(21) Appl. No.: 10/056,205

(22) Filed: Jan. 28, 2002

(65) Prior Publication Data

US 2002/0167667 A1    Nov. 14, 2002

Related U.S. Application Data

(63) Continuation-in-part of application No. 09/367,863, filed on Sep. 3, 1999, now Pat. No. 6,268,910, and a continuation-in-part of application No. 09/367,859, filed on Sep. 2, 1999.

(60) Provisional application No. 60/038,555, filed on Mar. 3, 1997, provisional application No. 60/038,554, filed on Mar. 3, 1997.

(51) Int. Cl.
*G01N 33/48*    (2006.01)
*G01N 21/00*    (2006.01)
*G01N 21/29*    (2006.01)

(52) U.S. Cl. ............... 356/39; 356/436; 422/82.09
(58) Field of Classification Search ............... 356/436, 356/39, 40, 43, 364, 73, 48; 374/159, 161, 374/126; 604/27, 28, 39, 43, 154, 66, 67, 604/320, 325; 435/4, 6, 7.6, 7.1
See application file for complete search history.

(56) References Cited

U.S. PATENT DOCUMENTS

| | | | |
|---|---|---|---|
| 3,737,096 A * | 6/1973 | Jones et al. | |
| 4,128,830 A * | 12/1978 | Weythman | |
| 4,522,494 A * | 6/1985 | Bonner | |
| 4,675,019 A * | 6/1987 | Bellhouse et al. | |
| 4,707,147 A * | 11/1987 | Aoki et al. | |
| 5,066,859 A * | 11/1991 | Karkar et al. | |
| 5,288,646 A * | 2/1994 | Lundsgaard et al. | |
| 5,291,884 A * | 3/1994 | Heinemann et al. | |
| 5,351,685 A | 10/1994 | Potratz | 128/633 |
| 5,353,790 A | 10/1994 | Jacques et al. | 128/633 |
| 5,360,004 A * | 11/1994 | Purdy et al. | |
| 5,366,903 A | 11/1994 | Lundsgaard et al. | 436/165 |
| 5,817,007 A * | 10/1998 | Fodgaard et al. | |

* cited by examiner

*Primary Examiner*—Zandra V. Smith
(74) *Attorney, Agent, or Firm*—Katten Muchin Rosenman LLP

(57) ABSTRACT

The present invention provides a method for determining a concentration of at least one analyte in a sample contained in a blood bag or in tubing in fluid communication with said blood bag, using an instrument comprising at least one calibration algorithm for the at least one analyte. The method comprises irradiating a sample in the tubing or the blood bag, using a near infrared and adjacent visible radiation source. Then measuring absorbance from the sample for the at least one analyte, and calculating a concentration of the at least one analyte using the absorbance and the at least one calibration algorithm.

8 Claims, 18 Drawing Sheets

METHOD AND APPARATUS FOR MEASURING ANALYTES IN BLOOD BAGS

This application is a Continuation-In-Part of U.S. application Ser. No. 09/367,863, filed Sep. 3, 1999, now U.S. Pat. No. 6,268,910 and U.S. application Ser. No. 09/367,859, filed Sep. 2, 1999, which claim priority from 60/038,555 and 60/038,554, respectively, both filed Mar. 3, 1997.

FIELD OF INVENTION

This invention relates to spectrophotometry and the spectrophotometric analysis of analytes in a blood bag, sample bag, or tubing. In particular, this invention relates to a method and apparatus for providing a rapid non-destructive measurement of one or more analytes in a blood bag or tubing by measurement of absorbance or reflectance.

BACKGROUND OF INVENTION

Blood is usually donated into sterile plastic bags that contain anticoagulants. These bags ("blood bags") are connected to one or more similar bags by plastic tubing in a closed system for maintaining sterility. After centrifugation of whole blood contained in a primary collection bag, plasma or plasma plus platelets can be separated from red blood cells in the bag: a higher centrifugal force can separate all cellular elements from the plasma, and a lower centrifugal force can separate the plasma plus platelets from the red cells; the plasma plus platelets can then be subjected to higher centrifugal force in order to separate the platelets from the plasma. Therefore, if separation of plasma, platelets, and red cells is required, a two step centrifugation is necessary, with a primary blood bag linked to two "satellite" bags in series. If separation of all cellular elements from plasma is required, a single-step centrifugation is necessary, with the primary blood bag linked to one satellite bag. In both cases, plasma will be contained in the last bag having transferred to this last blood bag via plastic tubing from the other bags.

Plasma is used frequently for transfusion to treat clotting disorders, to expand blood volume, to treat shock due to plasma loss in burns or hemorrhage. Plasma is also used frequently to prepare plasma substances, e.g., clotting factors, and other proteins like albumin. This process is referred to as plasma fractionation. The plasma used must not have excessive amounts of hemolysis, turbidity or bile pigments. Since donors are usually healthy, elevated bile pigments are not expected.

It is desirable to measure blood components, also referred to herein as analytes, that may be indicative, for example of disease state. These analytes may be determined in whole blood, serum, plasma, or in other solutions, for example buffer. In one such assay, red blood cells are separated from plasma by centrifugation, or red blood cells and various plasma proteins are separated from serum by clotting prior to centrifugation. Many tests conducted on plasma or serum samples employ a series of reactions which terminate after the generation of chromophores which facilitate detection by spectrophotometric measurements at one or two wavelengths. Elevated Hb in the blood, i.e., haemoglobinemia, can be due to disease states and as a result of specimen collection and handling. Elevated bile pigments can also be due to disease states. Increased lipid particles in the blood, also known as hyperlipidemia, can be due to disease states and dietary conditions. In blood banking, plasma containing certain undesirable or dangerous components will be discarded.

Although blood is screened for the presence of several viruses, there is no test which provides 100% assurance of the absence of these viruses, and there are still other harmful viruses which are never tested for. In order to increase assurance that harmful viruses are eradicated if present, viral inactivation processes are being developed. One method used for inactivating viruses in plasma is the addition of methylene blue (MB) to the plasma. Thus measurement of MB concentration may provide assurance that the plasma contains the required amount of MB.

Blood substitutes constitute another type of blood analytes. Blood substitutes are new products that are under development, for use instead of whole blood or red blood cells for transfusion. Most blood substitutes under development are made from human haemoglobin (Hb), but another type of blood substitute has been reported which is a milky-white emulsion containing tiny beads of perfluorocarbons wrapped in a surfactant. The former will create pseudohemolysis while the latter will create pseudolipemia, in serum and plasma specimens. Subunits of Hb-based blood substitute are chemically cross-linked for stability (cross-linked haemoglobin or CLHb) and produce absorbance spectra which are very similar to the absorbance spectra of normal Hb.

Blood transfusion is a life saving process performed after severe blood loss during trauma or surgery. Some advantages of using a blood substitute instead of blood or red blood cells are as follows: 1. blood substitutes are expected to be universally compatible with all blood types, therefore cross-matching will not be necessary; 2. maximum storage time of blood is 42 days, whereas blood substitutes could have a much longer shelf-life; 3. purification a blood substitute may include heat treatment, which may eliminate the threat of hazardous viruses such as HIV. However, a challenge blood substitutes will pose to the clinical laboratory is managing the effects of blood substitutes on blood tests. As described above, some blood substitutes will cause the appearance of pseudohaemolysis in serum or plasma specimens or will make these specimens appear as whole blood while other substitutes will cause the appearance of pseudolipemia.

Spectrophotometric measurement typically employs infrared (IR) or near infrared radiation (NIR) to assess the concentration of various constituents in a blood sample. Examples of photometric measurements using containers which hold a blood sample are disclosed in U.S. Pat. Nos. 5,291,884; 5,288,646; 5,066,859; and 5,366,903 (which are incorporated herein by reference).

U.S. Pat. No. 5,366,903 discloses a sampling device which allows photometric quantitative determination of an analyte in whole blood. The device overcomes the problems of having blood cells in a blood sample by effectively "squeezing out" red blood cells and providing a small volume of sample, free of red blood cell material, from which particular analytes can be measured.

Other applications of photometric methodology include non-invasive determinations of analyte concentrations such as described in U.S. Pat. Nos. 5,360,004; 5,353,790; and 5,351,685 (which are incorporated herein by reference). However none of these documents discloses a method of measuring blood analytes in a rapid fashion directly in the blood bag.

Current methods used for detecting haemoglobinemia, bilirubinemia, biliverdinemia and lipemia or turbidity utilize visual inspection of the specimen with or without comparison to a coloured chart. It is to be understood that those practising in the field use the terms lipemia and turbidity interchangeably. This is because lipemia is the major cause of turbidity in serum or plasma. In blood banking, turbidity is assessed by the ability to read print on a paper placed behind a plasma bag.

Screening of plasma specimens by visual inspection is semiquantitative at best, and highly subjective. Furthermore, visual inspection of plasma specimens is a time consuming, rate limiting process. Consequently, state-of-the-art blood analyzers in fully and semi-automated laboratories, and automated blood banking facilities cannot employ visual inspection of specimens.

Other methods to measure analytes employ direct spectrophotometric measurement of a diluted sample in a special cuvette. However, such methods are not rapid enough for screening samples. In order to obtain a measurement of the sample of the plasma or serum, specimen tubes must be uncapped, a direct sample of the specimen taken and diluted prior to measurement. Each of these steps is time-consuming and requires disposable cuvettes. In blood banking, sterile techniques must be practised; especially when blood products are not used promptly. Maintaining a closed system is necessary to avoid bacterial contamination, hence any screening for analytes must be performed with the bag-tubing system intact. Removing a segment of the tubing linking the blood/plasma bags by heat-sealing can be performed without altering the sterility of the blood products, but this too is time consuming. Therefore, a rapid and effective method for measuring analytes, including natural and non-natural compounds within plasma in the blood banking industry is required.

It is an object of the present invention to overcome disadvantages of the prior art. This object is met by a combination of the features of the main claims. The sub-claims disclose further advantageous embodiments of the invention.

SUMMARY OF THE INVENTION

This invention relates to spectrophotometry and the spectrophotometric analysis of analytes in a blood bag or tubing. In particular, this invention relates to a method and apparatus for providing a rapid non-destructive measurement of one or more analytes in a blood bag or tubing by measurement of absorbance or reflectance.

It is desirable to provide an apparatus and a method whereby the concentration of analytes in a blood sample in a blood bag, sample bag, or tubing in fluid communication with the blood or sample bag, is rapidly and accurately assessed without compromising the sterility of the sample, or destroying any of its components.

The present invention provides a method for determining a concentration of at least one analyte in a sample contained in a blood bag, sample bag, or in tubing in fluid communication with the blood bag or sample bag, using an instrument comprising at least one calibration algorithm for the at least one analyte, the method comprising:

a) irradiating the sample in the tubing, the blood bag, or the sample bag, using a radiation source from about 475 nm to about 2,700 nm;

b) measuring absorbance from the sample for the at least one analyte; and c) calculating a concentration of the at least one analyte using the absorbance and the at least one calibration algorithm.

The present invention also pertains to the method as defined above wherein in said step of calculating (step c)) combines first derivatives of at least two portions of a spectrum generated from the absorbance to provide the concentration.

Furthermore, the blood bag, sample bag, or the tubing used in the method as described above may be translucent and contain writing on its surface, and the irradiation is transmitted through the writing, the blood bag or the tubing, and the sample contained in the blood bag or the tubing.

The present invention also embraces the method defined above wherein the step of irradiating (step a)) includes reflecting radiation from a reflective surface placed behind the blood bag or the tubing.

The present invention includes the method defined above, wherein the at least one analyte is selected from the group consisting of haemoglobin, bilirubin, biliverdin, equivalent intralipid, methylene blue and cross-linked haemoglobin.

Furthermore the present iinvention provides a method for determining a concentration of one or more of haemoglobin, bilirubin, biliverdin, equivalent intralipid, methylene blue and cross-linked haemoglobin in a sample contained in a blood bag, sample bag, or in tubing in fluid communication with the blood bag or sample bag, using an instrument comprising one or more calibration algorithms for each of the haemoglobin, bilirubin, biliverdin, equivalent intralipid, methylene blue and cross-linked haemoglobin, the method comprising:

a) irradiating the sample in the tubing, the sample bag, or the blood bag using a radiation source of about 475 nm to about 2,700 nm;

b) measuring absorbance from the sample for the one or more of haemoglobin, bilirubin, biliverdin, equivalent intralipid, methylene blue and cross-linked haemoglobin; and c) calculating a concentration for one or more of the haemoglobin, bilirubin, biliverdin, equivalent intralipid, methylene blue and cross-linked haemoglobin using the absorbance and the one or more calibration algorithms, by combining first derivatives of at least two portions of a spectrum generated from the absorbance to provide the concentration.

This summary does not necessarily describe all necessary features of the invention but that the invention may also reside in a sub-combination of the described features.

BRIEF DESCRIPTION OF THE DRAWINGS

These and other features of the invention will become more apparent from the following description in which reference is made to the appended drawings wherein.

DESCRIPTION OF THE INVENTION

Figure 1:
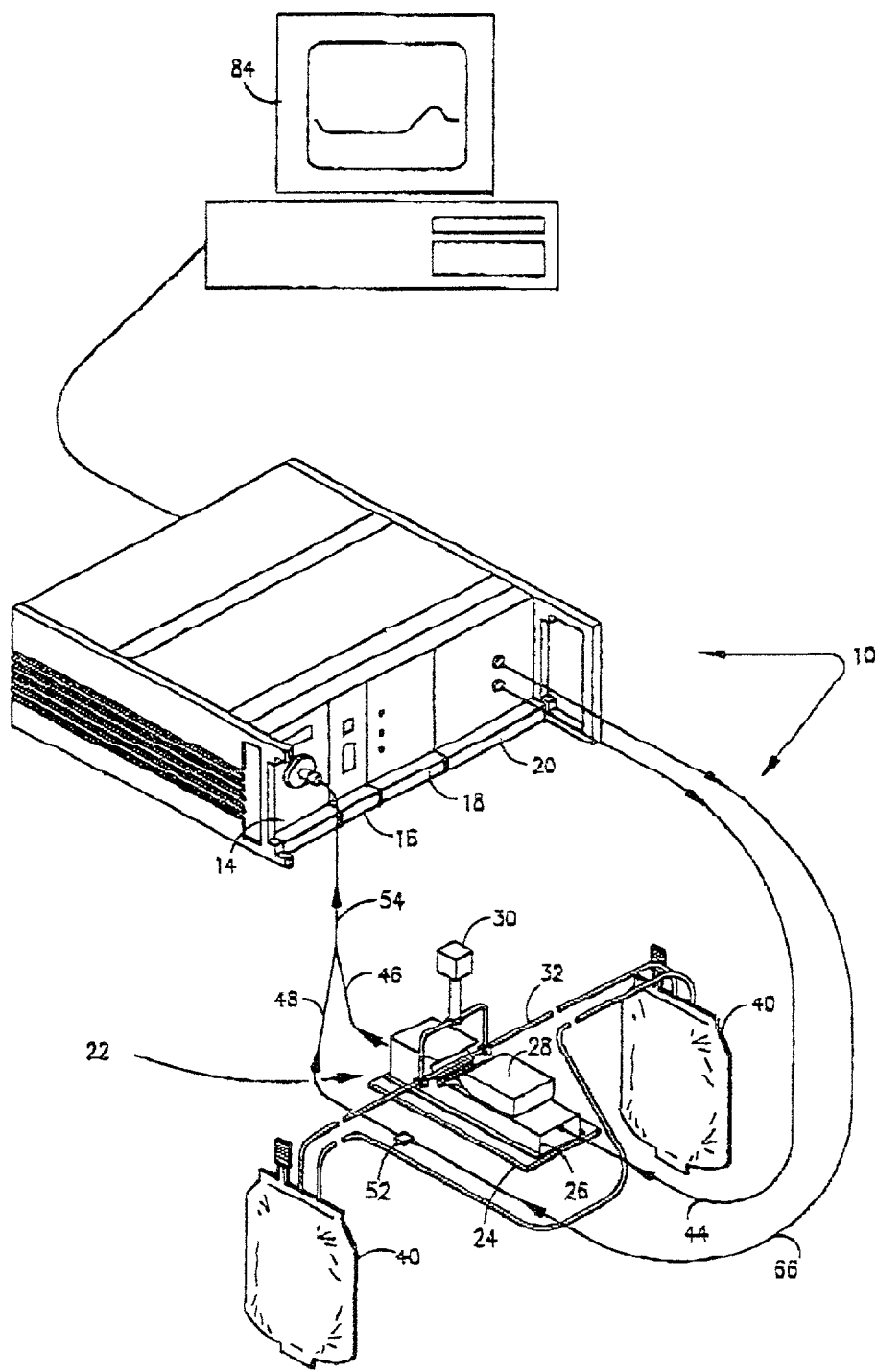
FIG. 1 is a perspective view of a system incorporating an apparatus of the present invention for analyzing blood analytes of a sample contained in blood bags.

This invention relates to spectrophotometry and the spectrophotometric analysis of analytes in a blood bag, sample bag, or tubing. In particular, this invention relates to a method and apparatus for providing a rapid non-destructive measurement of one or more analytes within a sample in a blood bag, or tubing, by measurement of absorbance or reflectance.

The following description is of a preferred embodiment by way of example only and without limitation to the combination of features necessary for carrying the invention into effect.

By "analyte" it is meant any chemical component present in a blood bag sample, whole blood, plasma, serum or other solution, for example a buffer, that may be detected with an apparatus and methods as described herein. For example, which is not to be considered limiting in any manner, an analyte may include:

1. Haemoglobin (Hb), for example for an assessment of haemolysis. Hb concentration may be determined by measurement of absorption of different wavelengths of light in specimens contained in a blood bag, sample bag, or tubing, and these values are then compared with values obtained through calibration using reference measurements for haemoglobin in similar specimens;

2. Bilirubin (BR), for example for an assessment of bilirubinemia. BR concentration may be determined by a combined measurement of absorption of different wavelengths of light in the bag or tubing specimens or samples, which are then compared with values obtained through calibration using reference measurements for BR in similar samples;

3. Biliverdin (BV), for example for an assessment of biliverdinemia. BV concentration may be determined by a combined measurement of absorption of different wavelengths of light in these specimens which are then compared with values obtained through calibration using reference measurements for BV in similar samples;

4. Intralipid™ (IL), for example for the assessment of turbidity; IL is a fat emulsion in water which is similar to naturally occurring chylomicrons, and may be used to simulate turbid serum or plasma specimens. Turbidity, in equivalent grams per liter IL may be determined by measurement of absorption of different wavelengths of light in the blood bag specimens which are then compared with values obtained through calibration using samples spiked with known amounts of IL;

5. Methylene blue (MB), for example as part of the viral inactivation quality assurance system. MB concentration may be determined by measurement of absorption of different wavelengths of light in a specimen, and comparing with values obtained through calibration using reference measurements for MB in similar specimens;

6. Cross-linked haemoglobin (CLHb) as a measure of the amount of blood substitute in plasma, a storage bag, blood bag, or tubing, as required. CLHb concentration may be determined by measurement of absorption of different wavelengths of light in a specimen and comparing these values with values obtained through calibration using reference measurements for CLHb in similar specimens. An example of a CLHb, which is not to be considered limiting in any manner, is Hemolink™; and other analytes as would be evident to one skilled in the art. On the basis of the results from measurements of any one or more of these analytes at a time, in comparison with reference measurements of various levels of analytes, disease state can be diagnosed or a decision can be made concerning the blood sample, for example, but not limited to whether to reject or accept plasma.

By "blood bag sample" it is meant a sample either obtained directly or indirectly from whole blood, or a solution, for example a buffered solution comprising one or more compounds, for example an analyte. Examples of a blood bag sample include, but are not limited to, whole blood, plasma, serum, or a buffered solution comprising one or more analytes. A blood bag sample may also be referred to as a sample or specimen.

Referring to FIG. 1, there is shown a non-limiting example of a system incorporating the apparatus of the present invention. The apparatus 10 comprises a spectrophotometer 14 optically coupled to a sample holder 22 through single optical fibres 44, 46. Sample holder 22, is shown in greater detail in FIGS. 2 and 3 and consists of a stationary part 26, and a movable part 28, mounted on a baseplate 24. Referring again to FIG. 1, apparatus 10 is mounted or installed adjacent to an automated blood banking system which may carry two or more blood bags 40 linked by polyvinylchloride (PVC) or other flexible tubing 32. However, tubing extending form only one blood bag may also be used as described herein. A robotic arm 30 may be installed to transport a section of the tubing 32 into the sample holder 22. It is understood that other conveyor transport mechanisms for tubing could be employed, a part of the blood bag can be used for sampling, and that all such variations are within the scope of the present invention. Furthermore, any means by which input and output fibre optic bundles are brought into alignment for measurement of absorption or reflectance in a blood specimen container are within the scope of the present invention.

Sample fibres 44 and 46 direct radiation from a light source to, and from, the sample respectively, and allow the bulk of the instrumentation to be placed remotely from the blood specimens. Multiple optical fibres 46 and 48 are the strands of a bifurcated optical fibre which collects radiation alternately from the sample and reference single optical fibre 66, and combines into one multiple optical fibre 54 which communicates with a spectrophotometer 14. Reference fibre 66 is joined to a strand 48 of the bifurcated fibre by a coupling 52.

After a sample is placed in holder 22, a sensor 34 will activate movable part 28 of the sample holder to close. Once in the closed position sample tubing 32 is held in cavity 42 of the sample holder. After a fixed time, which is required for the sample holder to close, light is transmitted through sample contained in tubing 32. Along the side of the sample holder is a separate fibre 66 for transmitting reference light, when shutter 56 (see FIG. 4) at the sample channel is closed and shutter 58 at the reference channel is open. Sample and reference dark scans are also performed with the sample in place with the sample holder closed, and shutters 56 and 58 closed, using the integration times used for the respective light scans.

Figure 2:
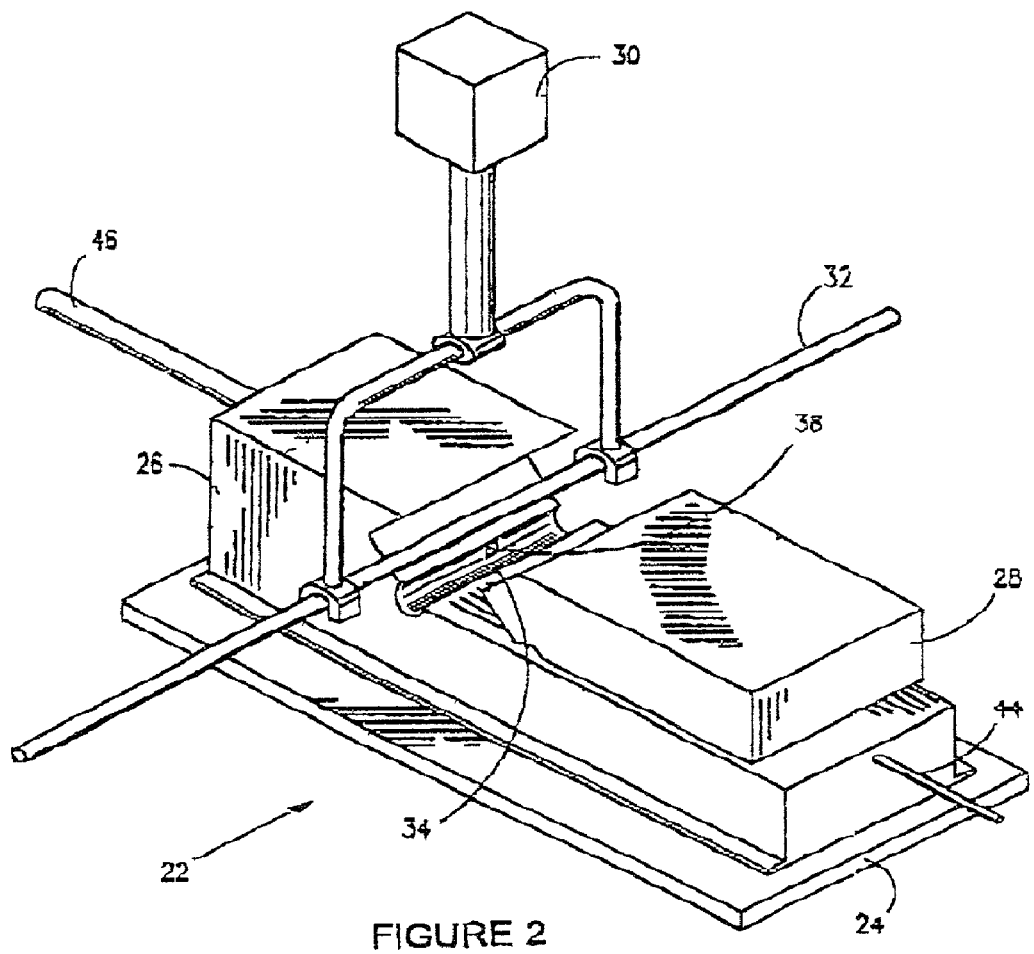
FIG. 2 is a perspective view of the sample holder of the apparatus of FIG. 1.
Figure 3:
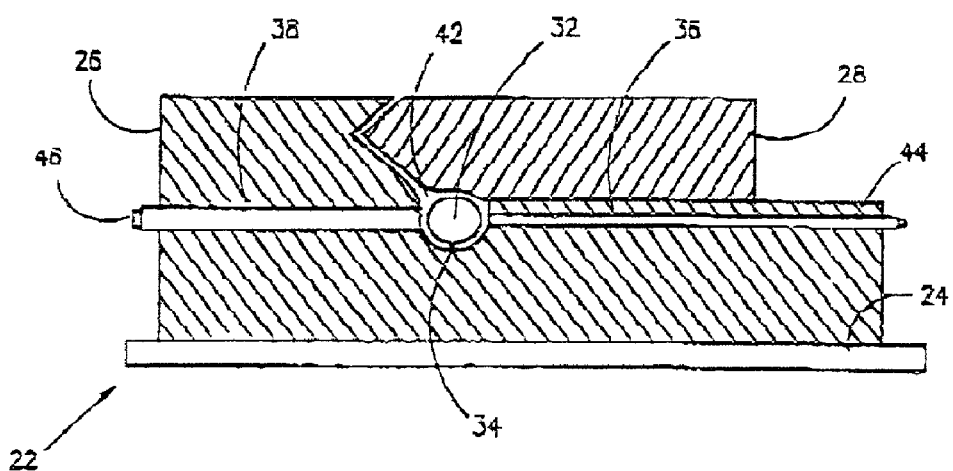
FIG. 3 is a longitudinal cross-sectional view of the sample holder of FIG. 1.

Referring to FIGS. 2 and 3, optical fibre 44 extends through a bore 36 in a wall of the sample holder as shown such that the end of optical fibre 44 communicates with cavity 42 to transmit radiation therein. Similarly, optical fibre 46 extends through a bore 38 in a wall of the sample holder opposite optical fibre 44. Fibre 46 communicates with cavity 42 to receive radiation impinging upon the portion of fibre 46 which communicates with cavity 42. In an alternative embodiment, optical fibers are arranged to permit measurement of reflected light in a sample.

Radiation is channelled through optical fibre 44 to the blood specimen in a section of tubing 32, and the radiation transmitted through the tubing and markings on the tubing, and blood specimen, is received by fibre 46, which returns collected radiation to spectrophotometer 14. Fibers 44, 46, 48 and 66 may be any suitable size, for example which is not to be considered as limiting, fibres 44 and 66 are both 0.4 millimeter diameter, and referring also to FIGS. 1 and 4, fibre 48 is 1.6 millimeters, and fibre 46 is 0.5 millimeter. The reference fibres 66 and 48, which are of different diameters, are coupled together by a coupler 52. Although specific sizes of these fibres have been identified it is understood by those skilled in the art that other fibre sizes could be employed.

Referring to FIG. 1, the apparatus 10 includes a spectrophotometer 14, a central processing unit 16, a power supply 18, and a lamp assembly module 20.

Figure 4:
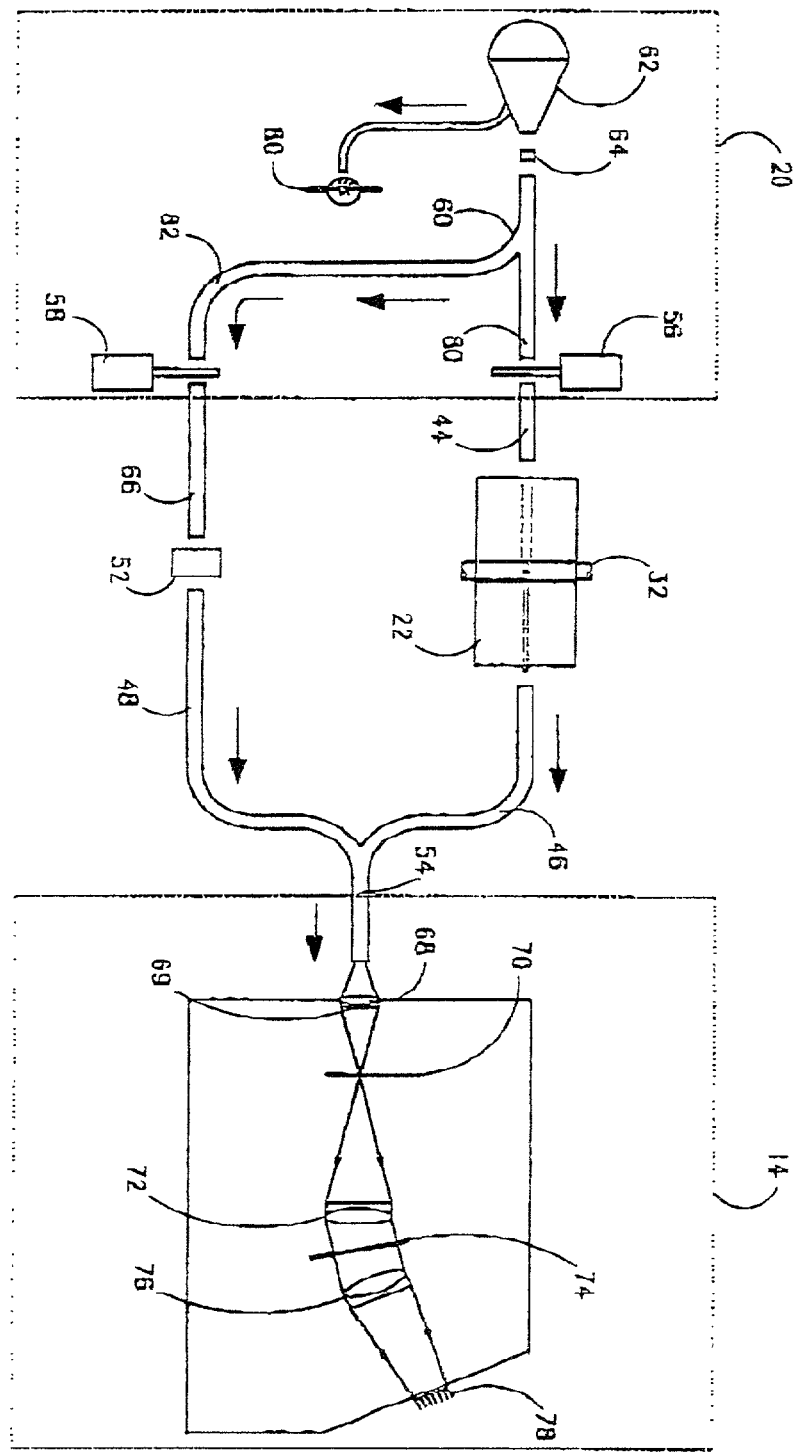
FIG. 4 is a schematic representation of elements of the apparatus of FIG. 1.

Referring to FIG. 4, the lamp assembly module 20 employs a light source 62. Preferably the light source is a quartz-tungsten-halogen 10 watt lamp, but other wattage lamps can be employed. The input power supply is alternating current, but the output to the light source is a stabilized direct current. Attached to the lamp is a photodetector 80, which monitors lamp output. Spectral output from light source 62 is broad band covering visible and NIR regions. Although the NIR region of the electromagnetic spectrum is generally considered to be the interval extending from 650 nm through to 2,700 nm, the nominal wavelength range of a preferred embodiment is from 475 nm to 2,700 nm, which is referred to herein as the "near infrared and adjacent visible region", and more preferably from about 475 nm to about 1075 nm. The beam of radiation from light source 62 is directed through a band-pass filter 64 and shaping filter 69 in the spectrophotometer 14. The band-pass filter is required to reduce unwanted radiation outside of 575–1075 nm or 475–910 nm, depending on the grating used. The shaping filter is also required to "flatten" the detection system's optical response. It should be understood that a particular grating will provide a particular wavelength range, and the band-pass and shaping filters are specific for the wavelength range. All data presented in this specification used a grating which produced 575–1075 nm wavelength range, except for the bilirubin data which used the 475–910 nm wavelength range. In a preferred embodiment, the 475–910 nm wavelength range is used because this range can be used for all the analytes discussed. The beam of radiation from filter 64 is transmitted through a bifurcated multi-optical fibre bundle 60 to provide sample and reference beams. In a preferred embodiment the active area of bundle 60 is 5.25 millimeters diameter. Bifurcated bundle 60 provides random sampling of lamp radiation to supply the sample and reference beams via two arms of 60, 80 and 82 respectively. In a preferred embodiment, a balanced emerging radiation is provided to the photo diode array (PDA) detector 78, from both the sample and reference paths, where 80 and 82 are 99% and 1% respectively, of the fibers of 60.

The sample and reference beams enter arms 46 and 48 respectively of a bifurcated multi-optical fibre bundle which combine in fibre 54 and are focused alternately onto a slit 70, by a focusing lens 68 and a shaping filter 69. Emerging radiation is collimated by lens 72 before the beam is directed to grating 74 which is a dispersing element which separates out component wavelengths. In a preferred embodiment dichromated gelatin is used as the grating material. Component wavelengths are focused by a lens 76, onto the PDA 78. Each element or pixel of the PDA is set to receive and collect a predetermined wavelength. In a preferred embodiment the PDA 78 comprises 256 pixels. The pixels are rectangular shaped to optimize the amount of optical radiation detected.

Spectrophotometer 14 is preferably a "dual-beam-in-time" spectrophotometer with a fixed integration time for the reference beam and a choice of integration time for the sample beam. Because the sample holder is not light-tight, sample and reference dark scans be subtracted from sample and reference light scans respectively; sample and reference dark scans are performed at the same integration times used for the respective light scans. In a preferred embodiment, the reference scan is performed at 13 milliseconds, and the sample scan is performed at 20 milliseconds; the maximum Analog to Digital Converter (ADC) value obtained at 20 milliseconds for a particular sample, is used to determine a new integration time up to 2600 milliseconds, such that saturation of the detector at any pixel does not occur. The maximum time allowed for any sample will depend on required speed of sample screening. Also, multiple scans can be averaged to minimize noise, but for the sake of speed in a preferred embodiment single scans are used.

When in use, each pixel or wavelength portion is measured approximately simultaneously during a particular scan. Optical radiation falling on each sensor element is integrated for a specified time and individual pixels or wavelengths are sampled sequentially by a 16 bit ADC.

Although the present embodiment details use of a PDA, any alternative means which achieves the same result is within the scope of the present invention. For example a filter-wheel system may be used. In carrying out measurements each analyte uses from one to four wavelengths or pixels. Given that the first derivative of absorbance with respect to measurements with the PDA is the difference between the absorbance at two adjacent pixels, the first derivative of absorbance at one wavelength with a filter-wheel system will require absorbance measured with two different narrow band-pass filters. It will be readily understood by those skilled in the art that the filters do not need to be assembled on a rotating wheel, but that any structure which achieves the result of a narrow band-pass filtration of absorbed radiation is within the scope of the present invention.

Thus in one embodiment of the present invention, the apparatus may comprise a quartz-tungsten-halogen bulb capable of emitting a near infrared, and adjacent visible region light beam having wavelengths from 475 nm to 1075 nm and a single optical fibre bundle which randomly samples light from the quartz-tungsten-halogen bulb. The single fibre bundle bifurcates into a sample path beam for travel along a sample path and a reference path beam for travel along a reference path. The bifurcated optical fibre consists of multiple fibres which focus random sampling of light from the lamp, into single fibres of 0.4 millimeter diameter for both the sample and reference beams. This apparatus further comprises two shutters, installed in the lamp assembly, for selectively blocking the sample path light beam which travels along the sample path through a sample enclosed in a housing, and the reference path light beam which travels along the reference path. The two light paths are collected into two fibres which converge into a single fibre which is focused onto the detector; the bifurcated collection optical fibre consists of multiple fibres. This apparatus further comprises a grating for dispersing the combined beam into component wavelengths which are passed onto the detector. The detector of this apparatus is a photodiode array (PDA) comprised of a plurality of pixels wherein each of the pixels is set to measure one of a plurality of predetermined light frequencies. Based on the measurement of the frequencies, the detector generates a plurality of signals wherein each of the signals is responsive to an amount of radiation received by each of the pixels. This apparatus further comprises an analog-to-digital converter to generate digital information from the plurality-of signals and a microprocessor, which is connected to the convertor, to correlate the digital information to a quantity of a known substance in the sample. In order to cover the 475 to 1075-nm wavelength range, one of two gratings must be used depending on in which range measurements are being taken: one grating provides 475–910 nm, and another grating provides 575–1075 nm.

Transmission is preferred over reflectance, although either may be used. Variations in apparent absorbance due to markings on tubing can be accounted for by using the first derivative of apparent absorbance. The term "apparent" absorbance is used because when the amount of light transmitted through a sample is measured, and transmitted light is converted to absorbance units (as shown below), light attenuation by any means other than that which is absorbed by the sample will be interpreted as absorbance. For example, lipid particles will scatter light away from the detector, and the scattered light will be interpreted as absorbance.

In a preferred embodiment, the PDA integrates optical radiation over a specified time and converts the optical signal to a time multiplexed analog electronic signal called a scan where absorbance is calculated as:

$$\text{Absorbance}_i = \log\{(\text{Reference Light}_i - \text{Reference Dark}_i)/(\text{Sample Light}_i - \text{Sample Dark}_i)\} + \log(ITS/ITR)$$

where:
Absorbance$_i$=Absorbance pixel i;
Reference Light$_i$=Reference pixel i readings, with reference path open and sample path closed by a shutter;
Reference Dark$_i$=Reference pixel i readings, with reference and sample paths closed by shutters;
Sample Light$_i$=Sample pixel i readings, with sample path open and reference path closed by a shutter;
Sample Dark$_i$=Sample pixel i readings, with sample and reference paths closed by shutters;
ITS=Integration time for sample measurement;
ITR=Integration time for reference measurement; and
i=the particular pixel (wavelength) in the PDA.

The electronic signal is proportional to the time that the detector integrates the optical signal. The electronic signal is amplified by analog electronic amplifiers and converted to a digital signal by an analog-to-digital converter or ADC. The digital information from the converter is interpreted for data analysis by a microprocessor 16 which is in turn connected via an RS232 connector to a computer 84. The results of the data analysis can be displayed on the computer 84, or on a printer (not shown in FIG. 1) connected to 84. A user can control the device through the computer 84, to specify a particular analyte to be analyzed and to determine the number and timing of measurements.

Although a rapid pre-screening device could take as much time as one to two minutes per sample measurement and still be considered rapid, the present invention allows for rapid pre-screening of samples by taking successive sample measurements at intervals of 5 seconds for the analytes to be measured, (not including analytes such as MB which will be measured after the analyte is added to the sample). After sample holder 22 is opened, the sample is placed according to a controlling process and a sensor in the sample holder activates the movable half of the holder to close when a sample is in place. Spectral data is collected after the holder is closed. Thereafter the sample is removed and another sample is picked up by the robotic arm and placed into the sample holder to allow for another measurement. This set of operations takes approximately 5 seconds.

The integration time for the sample beam is low for clear sample since there is less scattered light and therefore more light is transmitted to detector 78. When light is sufficiently scattered by, for example a turbid sample, spectrophotometer 14 automatically switches to a higher integration time. The higher integration time chosen will be within a pre-selected range, such that the detector's response is optimal. This feature will allow all samples, from the clearest to the most turbid, to be efficiently screened without exceeding the linear response range of the detector.

It is understood that this invention can be used with all varieties of tubing material or closely related material as typically encountered in the blood bag industry.

As with any quantitative method, calibration of the spectrophotometer is required. However the method for NIR calibration is much more complex than most which can be calibrated with a minimum of a single standard material of known concentration. In respect of NIR calibration, it is preferred that samples contain all components normally present during the analysis of an unknown sample; the sample preferably contains an even distribution of the analytes of interest, and it is preferred that the concentrations of any two analytes not correlate significantly. It is to be understood, that for any pre-screening of a typical sample for subsequent analysis, any combination of analytes may be present. The pre-screen allows for the determination of the concentration of any one analyte in the presence or absence of the others.

The first part of a process for generating a calibration curve in order to practice the method of the present invention is to store spectral data for a calibration set. A calibration algorithm for each analyte is installed in a microprocessor so that when an unknown sample is tested for a particular analyte the result is quickly produced.

In order to calculate the concentration of any analyte present, any one of several different methods, all of which are within the scope of this invention, may be used. For example, one method is to process raw absorbance measurements by multiple linear regression and choosing wavelengths using standard procedures and statistics to find optimal wavelengths at which to describe concentrations of analytes. However significant changes in the spectrum may be brought about by lipemia, for example, and influence the outcome of calculations for haemoglobin or for bilirubin, or biliverdin, or other analytes and consequently it is necessary to select additional wavelengths to compensate for these interactions.

Another method is to use all of the absorbance spectrum, and perform a suitable statistical analysis for example but not limited to either a principal component analysis or partial least squares analysis and effectively determine from the components that are optimised, the concentration of these different analytes. Unfortunately, these methods are computationally intensive and consequently take more time to calculate and increase the length of time required to assess each sample.

A preferred method is to calculate a first derivative of certain portions of absorbance spectra in respect of a particular analyte being measured. It is also possible to calculate the second, or third derivatives of absorbance, and such calculations are within the scope of this invention. However, each step of taking differences to calculate those derivatives is more time consuming and introduces more noise.

In practice, an optimal combination of first derivatives of at least two portions of an absorbance spectrum generated from a scan of a blood specimen containing a particular analyte, is used to calculate analyte concentration. The precise approach used depends on the analyte being measured.

Calibration algorithms were developed for six analytes namely, haemoglobin, bilirubin, biliverdin, intralipid, methylene blue, and cross-linked haemoglobin based on wavelengths in the 475 to 910-nm range. However, if BR measurement is not required, the grating which provides 575–1075 nm can be used. In one aspect of the present invention, more than one calibration algorithm can be developed for the same analytes, using different wavelengths. This is exemplified by the two different calibration algorithms for IL, shown later.

In one aspect of the invention any analyte can be measured for example but not limited to Haemoglobin (Hb), Bilirubin (BR), Biliverdin (BV), Intralipid™, Methylene blue (MB), and Cross-linked haemoglobin (CLHb).

Hb concentration may be determined by measurement of absorption of different wavelengths of light in blood specimens contained in a blood bag that are then compared with values obtained through calibration using reference measurements for haemoglobin in similar specimens.

Turbidity, in equivalent grams per liter Intralipid™ (IL), may be determined by measurement of absorption of different wavelengths of light in the blood bag specimens which are then compared with values obtained through calibration using samples spiked with known amounts of IL.

BR concentration may be determined by a combined measurement of absorption of different wavelengths of light in the blood bag blood sample that are then compared with values obtained through calibration using reference measurements for BR in similar samples.

BV concentration may be determined by a combined measurement of absorption of different wavelengths of light in a specimen or sample which is then compared with values obtained through calibration using reference measurements for BV in similar samples.

MB concentration may be determined by measurement of absorption of different wavelengths of light in blood specimens which are then compared with values obtained through calibration using reference measurements for MB in blood specimens.

CLHb concentration may be determined by measurement of absorption of different wavelengths of light in blood specimens or samples which are then compared with values obtained through calibration using reference measurements for CLHb in similar specimens.

On the basis of the results from measurements of any one or more of these analytes at a time, in comparison with reference measurements of various levels of analytes, disease states can be diagnosed or a decision can be made concerning whether to reject or accept the blood sample. Instead of using a reference measurement for a substance, its actual concentration can be calculated from the known amount that was added.

In another embodiment, light is allowed to be reflected off a reflecting surface placed directly behind the blood sample contained in a blood bag.

In this manner, Hb concentration can be determined by measurement of reflectance of different wavelengths of light in the blood bag blood specimens which are then compared with values obtained through calibration using reference measurements for haemoglobin in similar samples.

Turbidity, in equivalent g/L IL, may be determined by measurement of reflectance of different wavelengths of light in blood specimens which are then compared with values obtained through calibration using samples spiked with known amounts of IL.

BR concentration may be determined by a combined measurement of reflectance of different wavelengths of light in blood specimens which are then compared with values obtained through calibration using reference measurements for BR in similar samples.

BV concentration may be determined by a combined measurement of reflectance of different wavelengths of light in blood specimens which are then compared with values obtained through calibration using reference measurements for BV in similar samples.

MB concentration may be determined by measurement of reflectance of different wavelengths of light in blood specimens which are then compared with values obtained through calibration using reference measurements for MB in similar specimens.

CLHb concentration may be determined by measurement of reflectance of different wavelengths of light in blood specimens which are then compared with values obtained through calibration using reference measurements for CLHb in similar specimens.

On the basis of the results from measurement of any one or more of these analytes at a time, in comparison with reference measurements of various levels of analytes, disease state can be diagnosed or a decision is made concerning whether to reject or accept the blood sample contained in the blood bag.

Therefore, the present invention provides a method for determining the concentration of one or more analytes in a blood bag, sample bag or tubing in fluid communication with the blood bag or sample bag, wherein the method comprises: transmitting a beam of radiation along a sample path through a sample in a blood bag or tubing, and along a reference path by-passing the sample; selectively receiving the beam of radiation from the sample path and the reference path, and analyzing the received beams of radiation from the sample path and from the reference path for an amplitude of at least one predetermined light frequency; and correlating the absorbance of an analyte at least one predetermined light frequency with its concentration. Preferably, the concentration of one or more analytes in a bag or tubing are selected from a group comprising but not limited to haemoglobin, bilirubin, Intralipid, biliverdin, methylene blue and cross-linked haemoglobin.

There is also provided a method for determining the concentration of at least one analyte in blood bag sample contained in one or more blood or stage bags, or within tubing that is in fluid communication with a blood bag, the method comprising the steps of:
(A) providing the tubing and connecting one or more bags, such that the blood sample can flow from the bag into the tubing;
(B) providing a lamp to irradiate the blood sample in the tubing;
(C) providing elements for directing radiation into the tubing and elements for receiving radiation from the tubing such that a constant fixed optical path length is established between the elements for directing and the elements to receive radiation across the tubing and sample;
(D) irradiating the tubing;
(E) providing a spectrophotometer to measure radiation from the tubing; and
(F) calculating a concentration of the at least one analyte based on the measurement to provide the concentration.

There is also provided a method for determining the concentration of at least one analyte in a blood sample contained in a blood collection bag, the method comprising the steps of:
(A) providing a blood collection bag containing the sample;
(B) providing a lamp to irradiate the sample in the bag;
(C) providing elements for directing radiation into the bag; elements for receiving radiation from the bag such that a constant fixed optical path length is established from the elements to direct to the elements to receive radiation across the bag and sample;
(D) irradiating the bag;
(E) providing a spectrophotometer to measure radiation from the bag; and
(F) calculating a concentration of the at least one analyte based on the measurement to provide the concentration.

As will be readily understood by those skilled in the art, several algorithms can be developed for each analyte using different groups of wavelengths with the resultant prediction performance by the different algorithms for the same analyte being similar. Also, algorithms can be developed for any analyte or combinations of analytes including blood substitutes, which will enable one to adjust measured analyte concentrations, for the presence of one or more analytes.

The present invention will be further illustrated in the following Examples. However, it is to be understood that these examples are for illustrative purposes only and should not be used to limit the scope of the present invention in any manner.

EXAMPLES

In respect of Hb, results may be obtained by calculating the first derivative of absorbance measurements at wavelengths of approximately 591 nm and 653 nm. In respect of turbidity, results may be obtained by calculating the first derivative of absorbance measurements at wavelengths of approximately 988 nm and 1038 nm, or for an alternative algorithm, 874 nm. In respect of bile pigments, results may be obtained by calculating the first derivative of absorbance measurements at wavelengths of approximately 649 nm 731 nm and 907 nm for BV, and 504 nm, 518 nm and 577 nm for BR. In respect of MB results may be obtained by calculating the first derivative of absorbance measurements at wavelengths of approximately 677 nm and 953 nm. In respect of Hemosol™ CLHb, optimal results may be obtained by calculating the first derivative of absorbance measurements at wavelengths of approximately 541 nm, 558 nm, 600 nm and 616 nm.

Since turbidity or lipemia is mainly due to chylomicron particles, turbidity may be simulated by adding IL to clear plasma; IL is an emulsion of fat particles similar to naturally-occurring chylomicrons.

Calibration equations outlined below cover a broad range of variability anticipated in the concentration of the analytes. According to the present invention, if low-end accuracy becomes a concern, separate calibrations can be developed: one for the high end, and a second, if the result predicted by the previous calibration is less than a predetermined level.

To calibrate spectrophotometer for use in a preferred embodiment of the present invention, for haemoglobin, IL and BV plasma specimens with normal appearance were spiked with 0 to 6 g/L Hb, 0 to 6.5 g/L IL, and 0 to 4.5 mg/dL BV. No significant intercorrelation among the analytes was allowed. The specimens were run once immediately after preparation, and then repeated using different segments of polyvinylchloride (PVC) tubing with random location of white markings on the surface of the tubing. Hb was prepared by replacing normal plasma (by appearance) with water and lysing erythrocytes through three freeze-thaw cycles. The Hb content of the supernatant of the lysate was measured on an Abbott Cell Dyn™. The spectra were stored on diskettes. Analyses on sample sets were performed by a statistical computer program and algorithms developed for Hb, IL and BV. Independent sample sets were set aside for validation (referred to in the graphical representations as prediction) of the calibration equations. BR does not affect the measurements of Hb, IL and BV at their respective calibration wavelengths.

Figure 5:
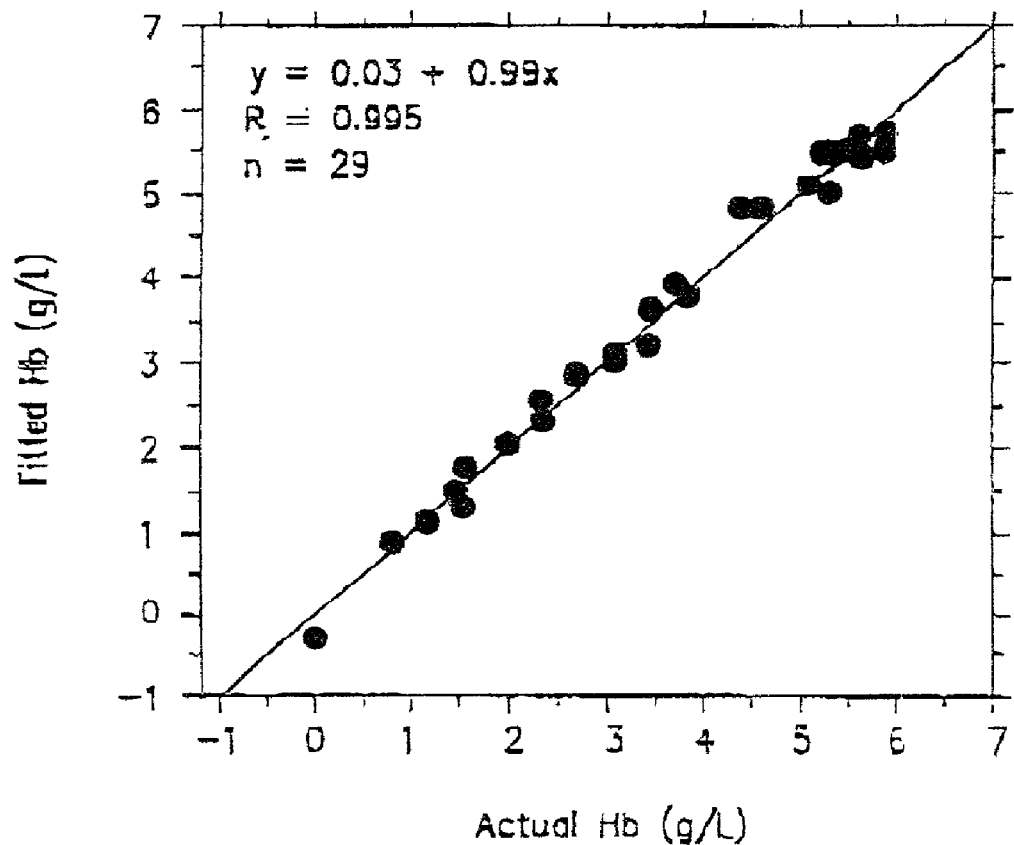
FIG. 5 is a graphic representation of a linear regression fit of data for haemoglobin calibration in units of grams per liter on the abscissa and ordinant axes

FIG. 5 is a graphic representation of a linear regression fit of the data generated from the Hb calibration. The algorithm which was developed for Hb based on this data is as follows:

$$\text{g/L } Hb = 45.68(591 \text{ nm}) - 47.48(653 \text{ nm}) - 0.42$$

where the numbers in front of the parentheses on the right hand side of the equation are the first derivative of the absorbance measured at the wavelength specified in the parentheses.

Figure 6:
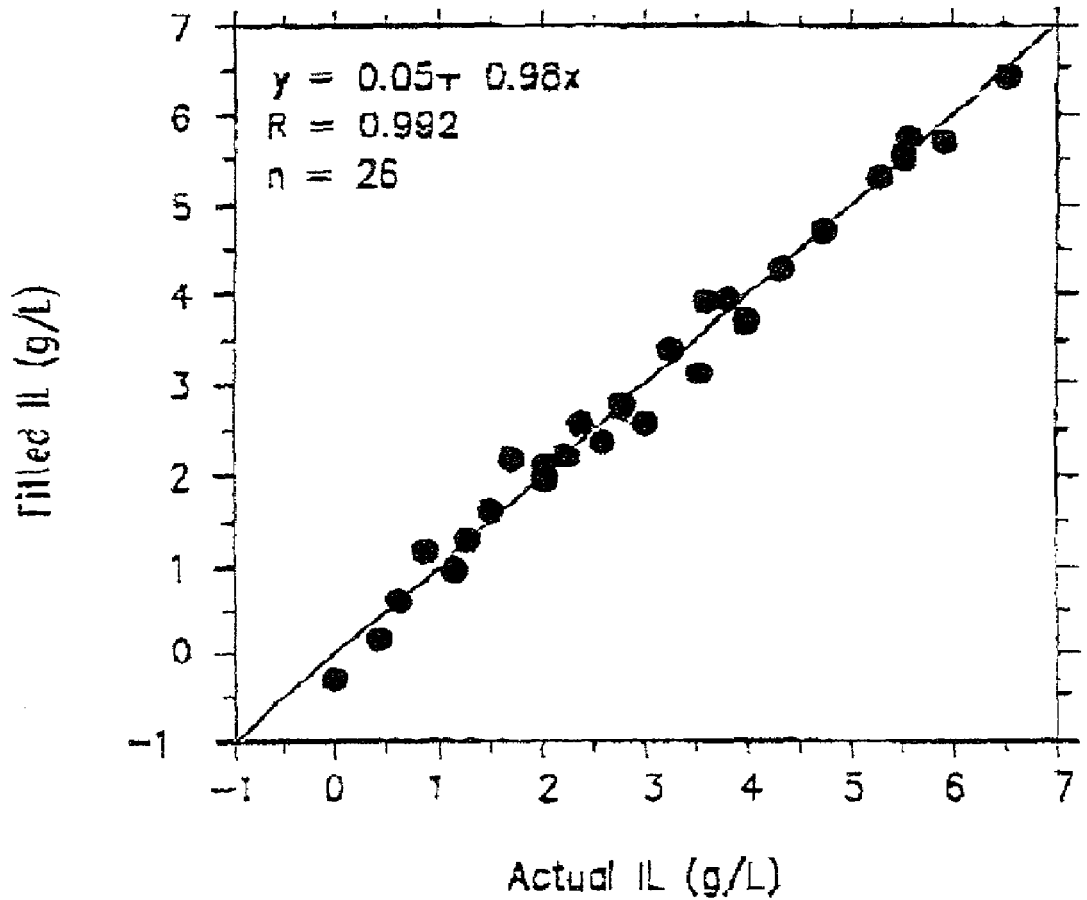
FIG. 6 is a graphic representation of a linear regression fit of data for turbidity calibration (using 988 nm and 1038 nm) in terms of intralipid concentration in units of grams per liter on the abscissa and ordinant axes.

FIG. 6 is a graphic representation of a linear regression fit of the data generated from the IL calibration. The algorithm which was developed for IL based on this data is as follows:

$$\text{gIL } IL = 432.42(988 \text{ nm}) + 40.40(1038 \text{ nm}) + 0.04$$

where the numbers in front of the parentheses on the right hand side of the equation are the first derivative of the absorbance measured at the wavelength specified in the parentheses.

Figure 7:
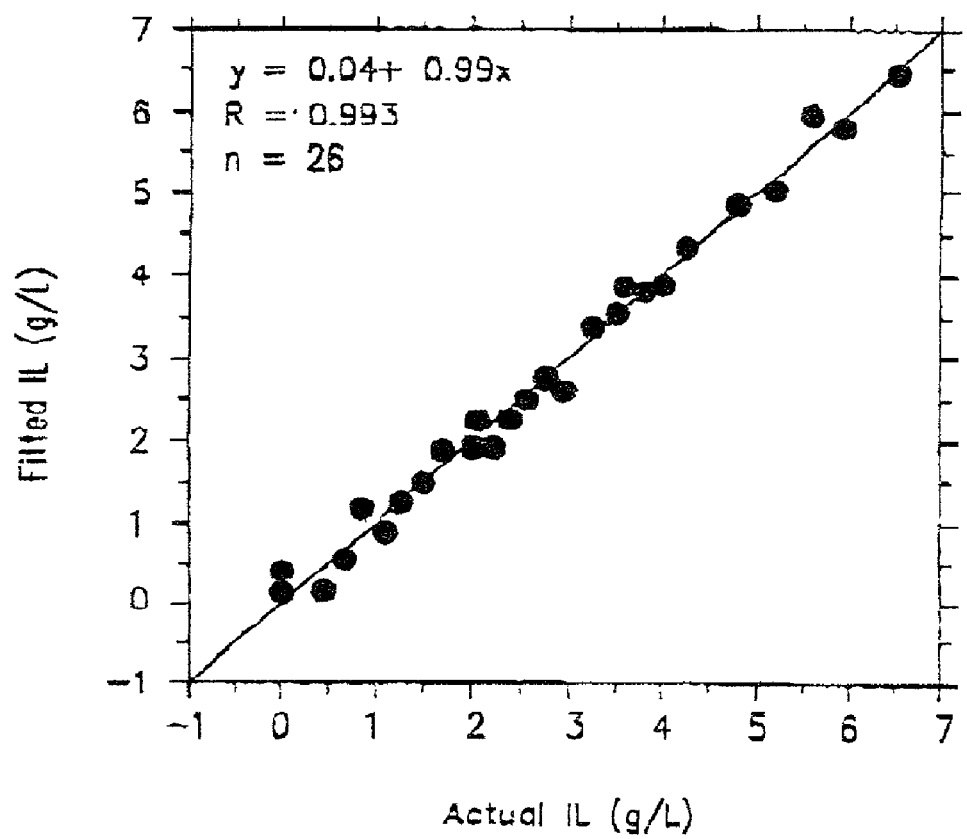
FIG. 7 is a graphic representation of a linear regression fit of data for turbidity calibration (using 874 nm) in terms of intralipid concentration in units of grams per liter on the abscissa and ordinant axes.

FIG. 7 is a graphic representation of a linear regression fit of the data generated from another IL calibration. The alternative algorithm which was developed for IL based on this data is as follows $$\text{g/L } IL = 305.78(874 \text{ nm}) + 1.12$$

where the numbers in front of the parentheses on the right hand side of the equation are the first derivative of the absorbance measured at the wavelength specified in the parentheses.

Figure 8:
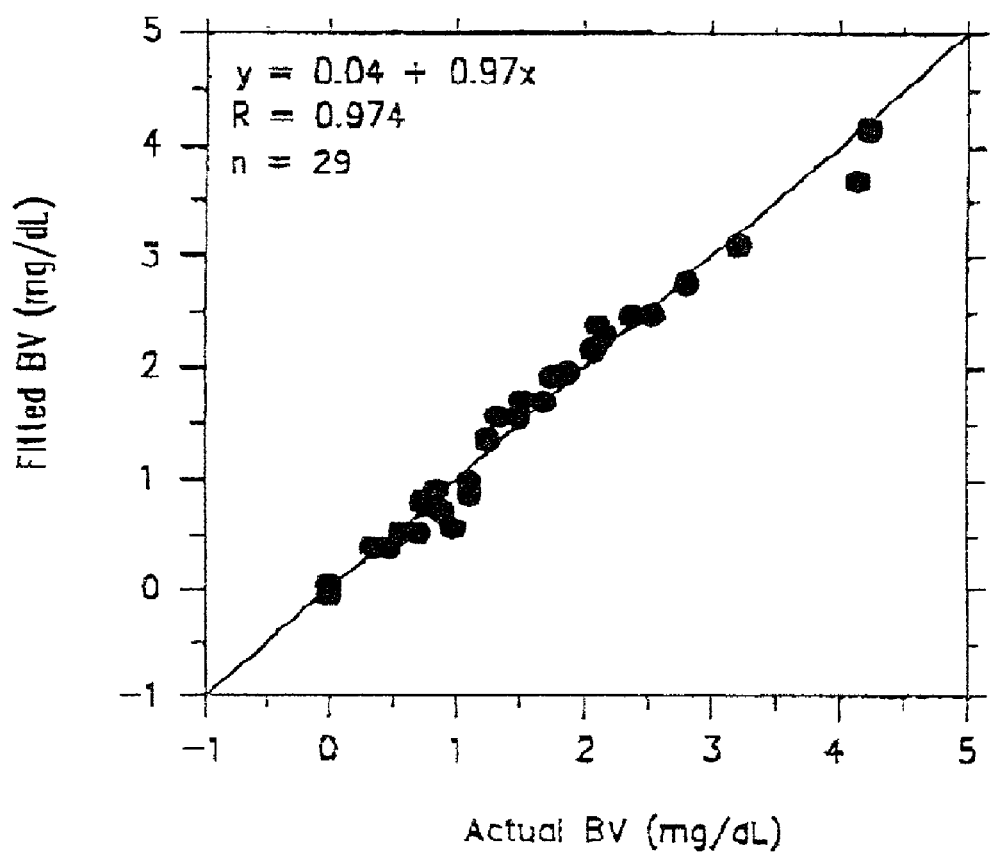
FIG. 8 is a graphic representation of a linear regression fit of data for biliverdin calibration in units of milligrams per deciliter on the abscissa and ordinant axes.

FIG. 8 is a graphic representation of the results of a linear regression fit of the data generated from the BV calibration. The algorithm which was developed for BV based on this data is as follows:

$$\text{mg/dL } BV = -45.40(649 \text{ nm}) + 323.15(731 \text{ nm}) - 493.79 (907 \text{ nm}) - 1.14$$

where the numbers in front of the parentheses on the right hand side of the equation are the first derivative of the absorbance measured at the wavelength specified in the parentheses.

In order to calibrate the spectrophotometer for BR, plasma specimens with normal appearance were spiked with 0 to 42 mg/dL Ditaurobilirubin (a synthetic conjugated bilirubin used to calibrate chemistry analyzers), 0 to 3 g/L Hb, 0 to 3 g/L IL, and 0 to 4 mg/dL BV. No significant intercorrelation among the analytes was allowed. The specimens were run once, immediately after preparation, and then repeated using different segments of PVC tubing with random location of white markings on the surface of the tubing. Hb was prepared by replacing normal plasma (by appearance) with water and lysing erythrocytes through three freeze-thaw cycles. Hb content of the supernatant of the lysate was measured on an Abbott Cell Dyn.™ The spectra were stored on diskettes. The analyses on sample sets were performed by a statistical computer program and algorithms developed for BR. Independent sample sets were set aside for validation (referred to in the graphical representations as prediction) of the calibration equations.

Figure 9:
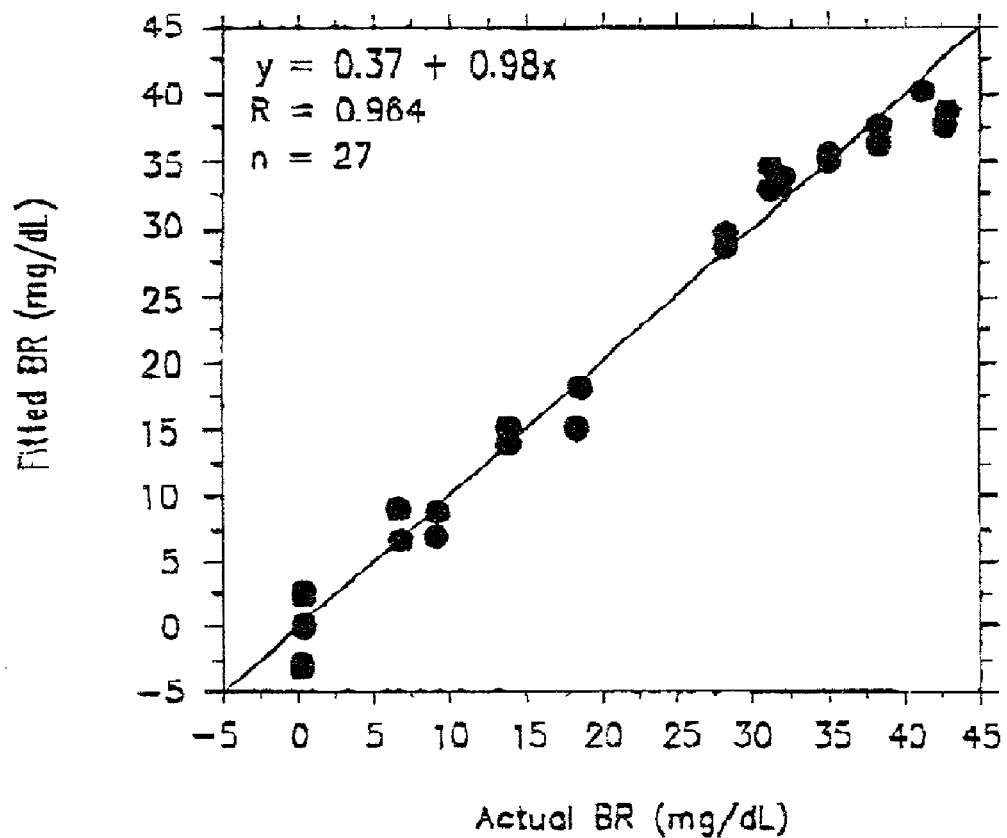
FIG. 9 is a graphic representation of a linear regression fit of data for bilirubin calibration in units of milligrams per deciliter on the abscissa and ordinant axes.

FIG. 9 is a graphic representation of the results of a linear regression fit of the data generated from the BR calibration. The algorithm which was developed for BR based on this data is as follows:

$$\text{mg/dL } BR = -43.03(504 \text{ nm}) + 252.11(518 \text{ nm}) + 240.03 (577 \text{ nm}) - 2.89$$

where the numbers in front of the parentheses on the right hand side of the equation are the first derivative of the absorbance measured at the wavelength specified in the parentheses.

To calibrate the spectrophotometer for methylene blue, plasma specimens with normal plasma (by appearance) were spiked with 0 to 860 $\mu$g/dL MB. In practice, MB is only added to plasma with normal appearance, therefore calibration for MB does not require the presence of the other analytes that may interfere with measurements. The specimens were run once, immediately after preparation, and then repeated using different segments of PVC tubing with random location of white markings on the surface of the tubing. The spectra were stored on diskettes. The analyses on sample sets were performed by a statistical computer program and algorithms developed for MB. Independent sample sets were set aside for validation (referred to in the graphical representations as prediction) of the calibration equations. It should be understood that a calibration equation for MB in the presence of other analytes, can be developed according to the method of the present invention if necessary.

Figure 10:
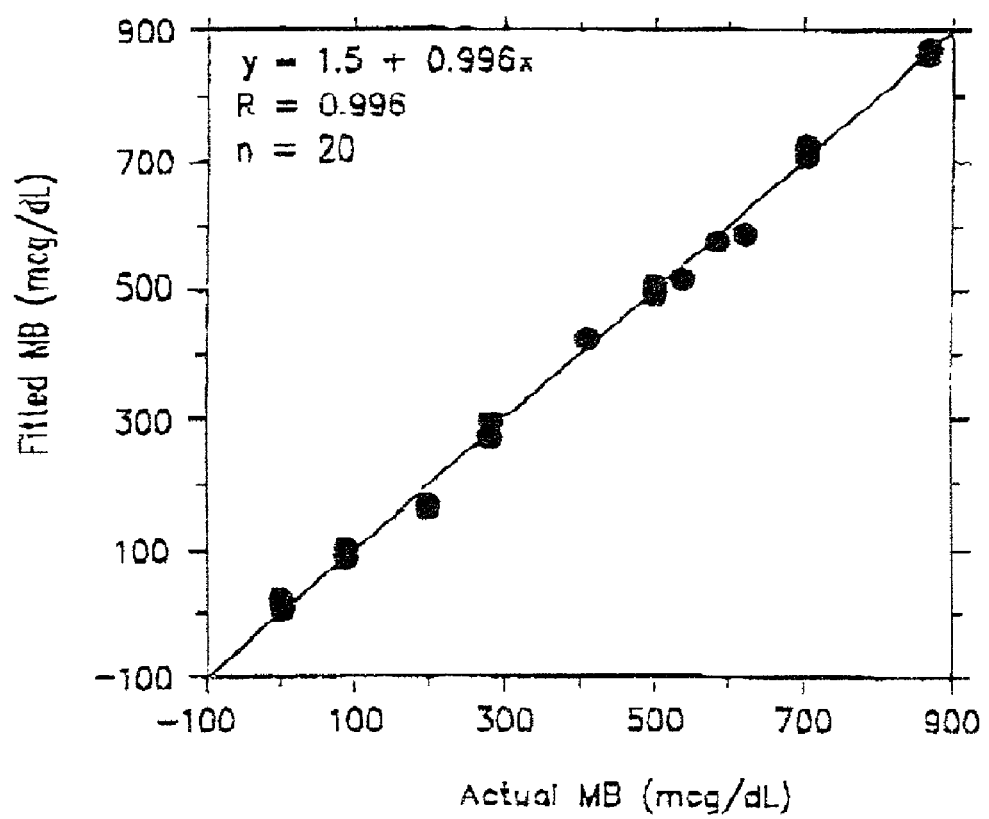
FIG. 10 is a graphic representation of a linear regression fit of data for methylene blue calculation in units of micrograms per deciliter (mcg/dL) on the abscissa and ordinant axes.
Figure 11:
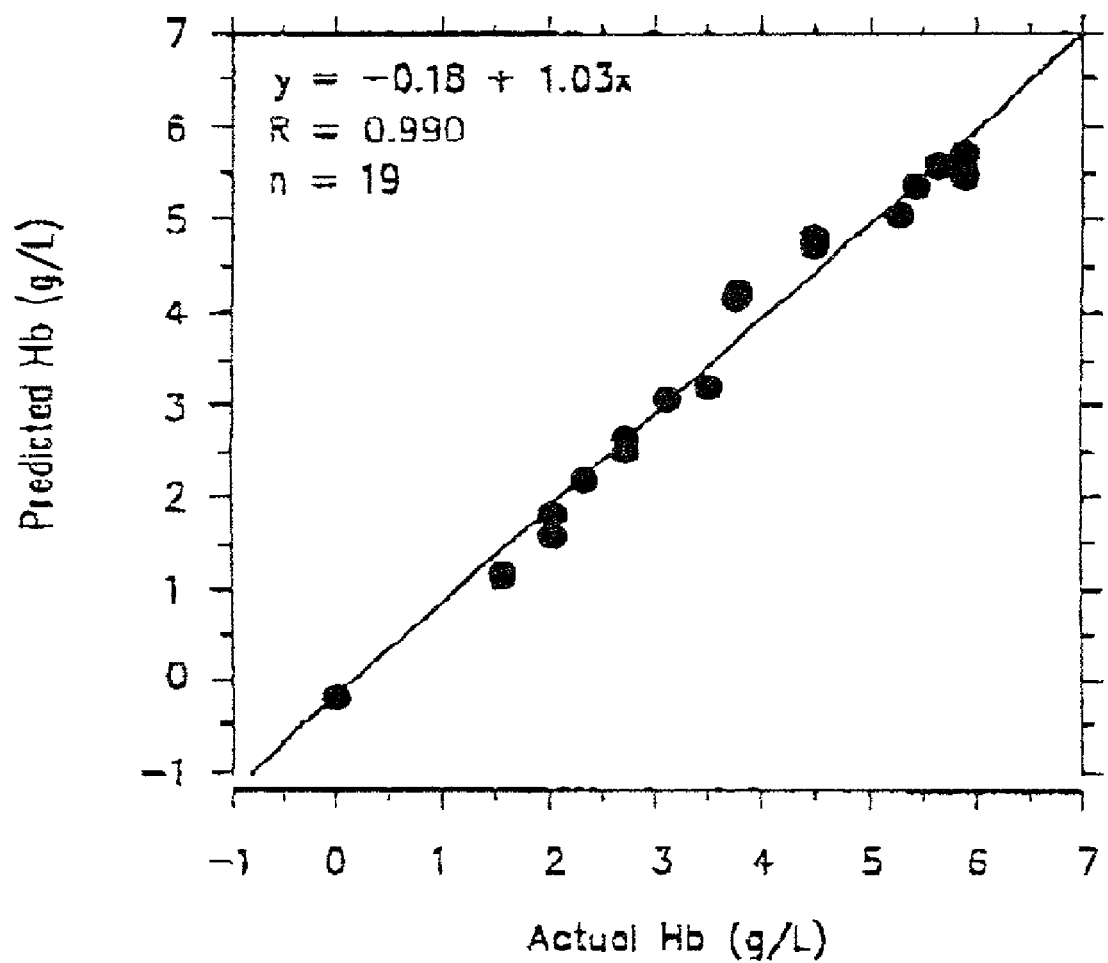
FIG. 11 is a graphic representation of a linear regression fit of data in respect of predicted haemoglobin concentration for samples not used in the calibration process, in units of grams per liter on the abscissa and ordinant axes.
Figure 12:
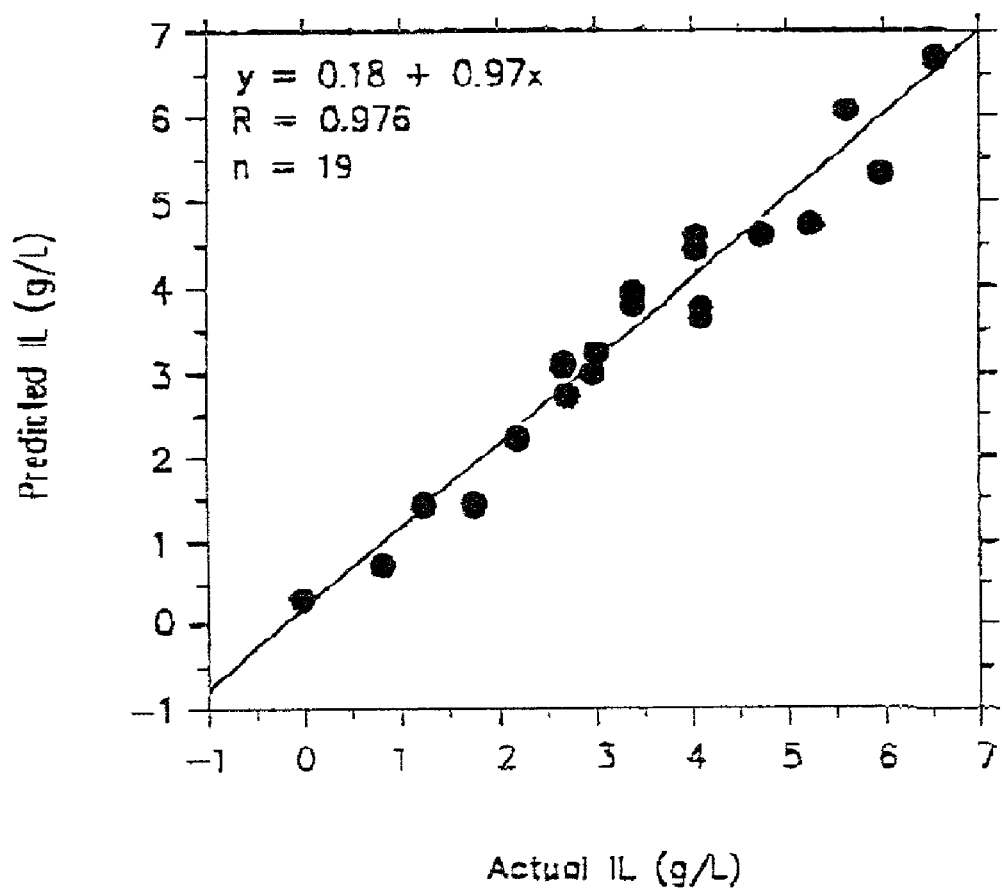
FIG. 12 is a graphic representation of a linear regression fit of data in respect of predicted intralipid concentration for samples not used in the calibration (using 988 nm and 1038 nm) process, in units of grams per liter on the abscissa and ordinant axes.
Figure 13:
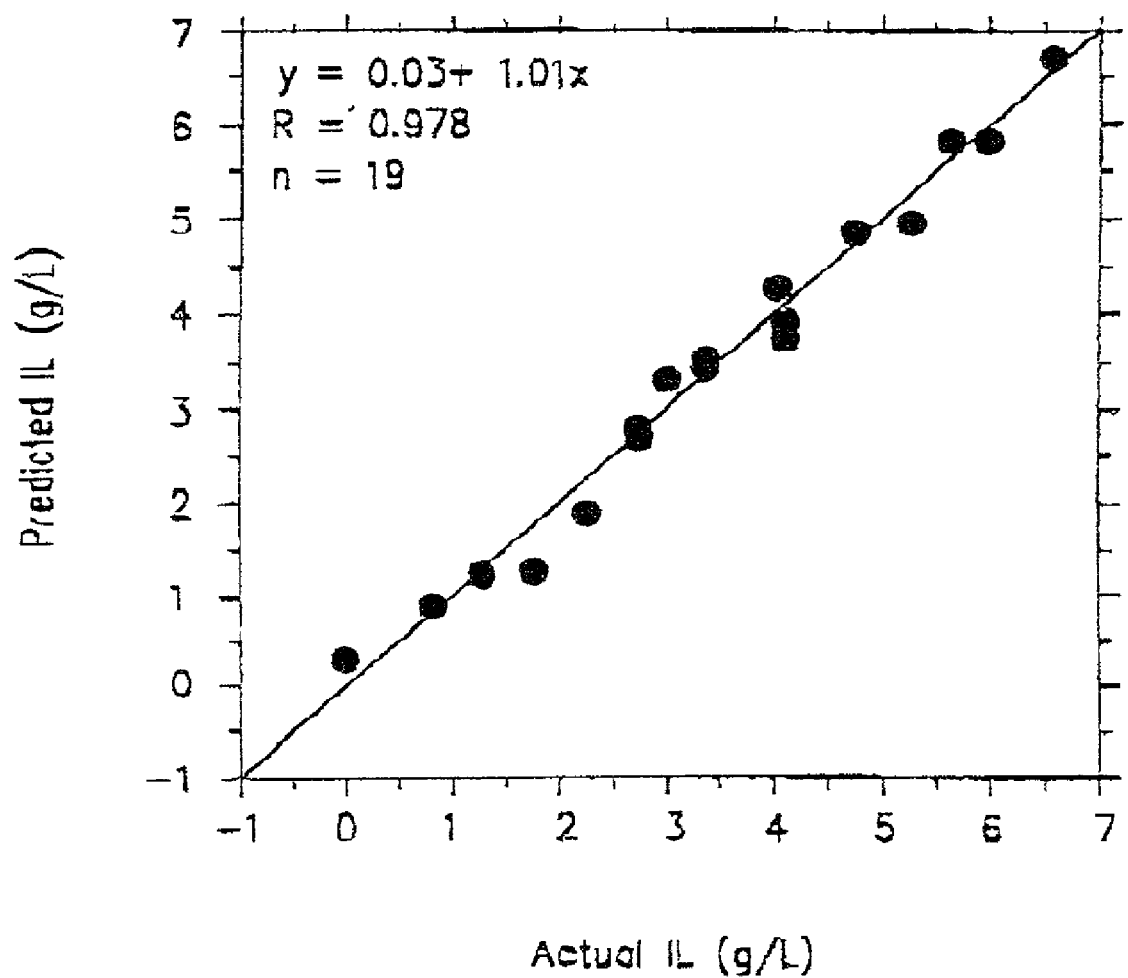
FIG. 13 is a graphic representation of a linear regression fit of data in respect of predicted intralipid concentration for samples not used in the calibration (using 874 nm) process, in units of 15 grams per liter on the abscissa and ordinant axes.
Figure 14:
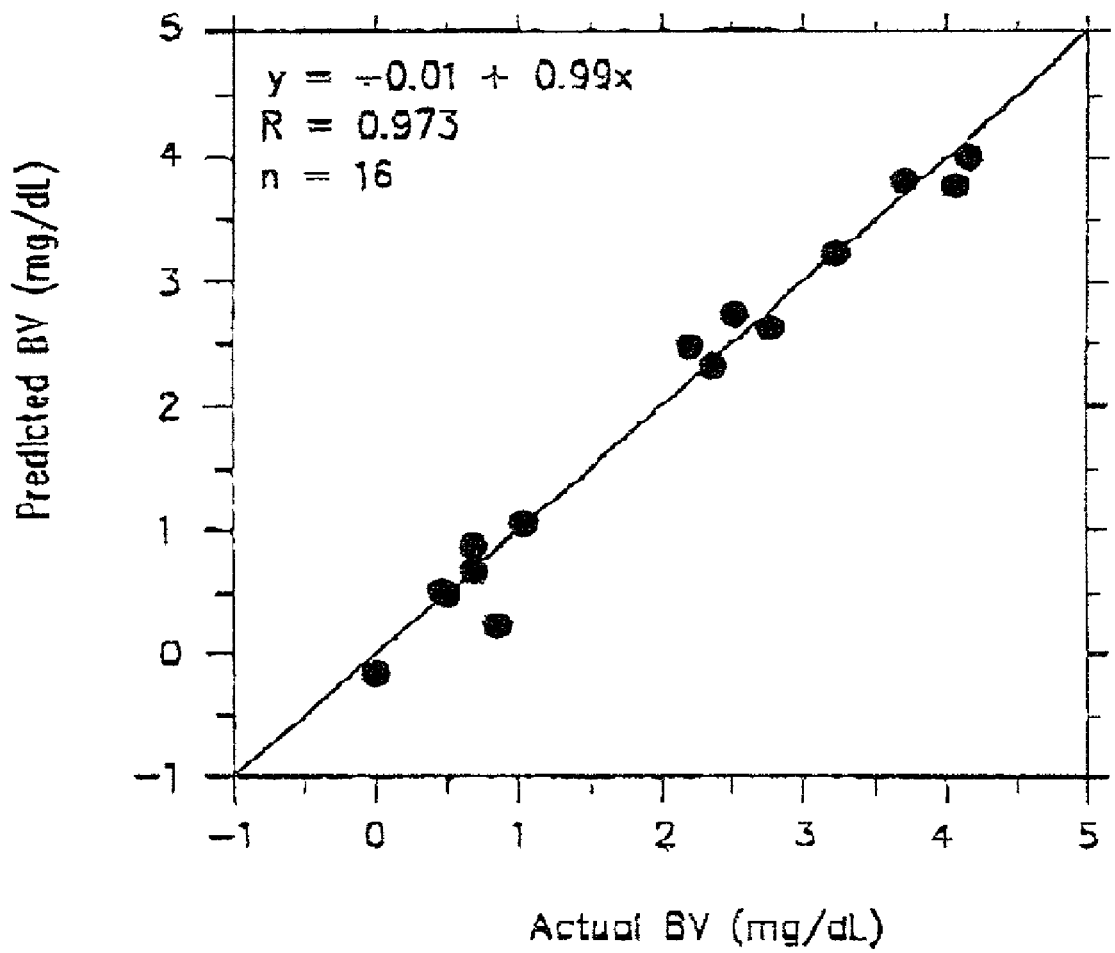
FIG. 14 is a graphic representation of a linear regression fit of data in respect of predicted biliverdin concentration for sample not used in the calibration process, in units of milligrams per deciliter on the abscissa and ordinant axes.
Figure 15:
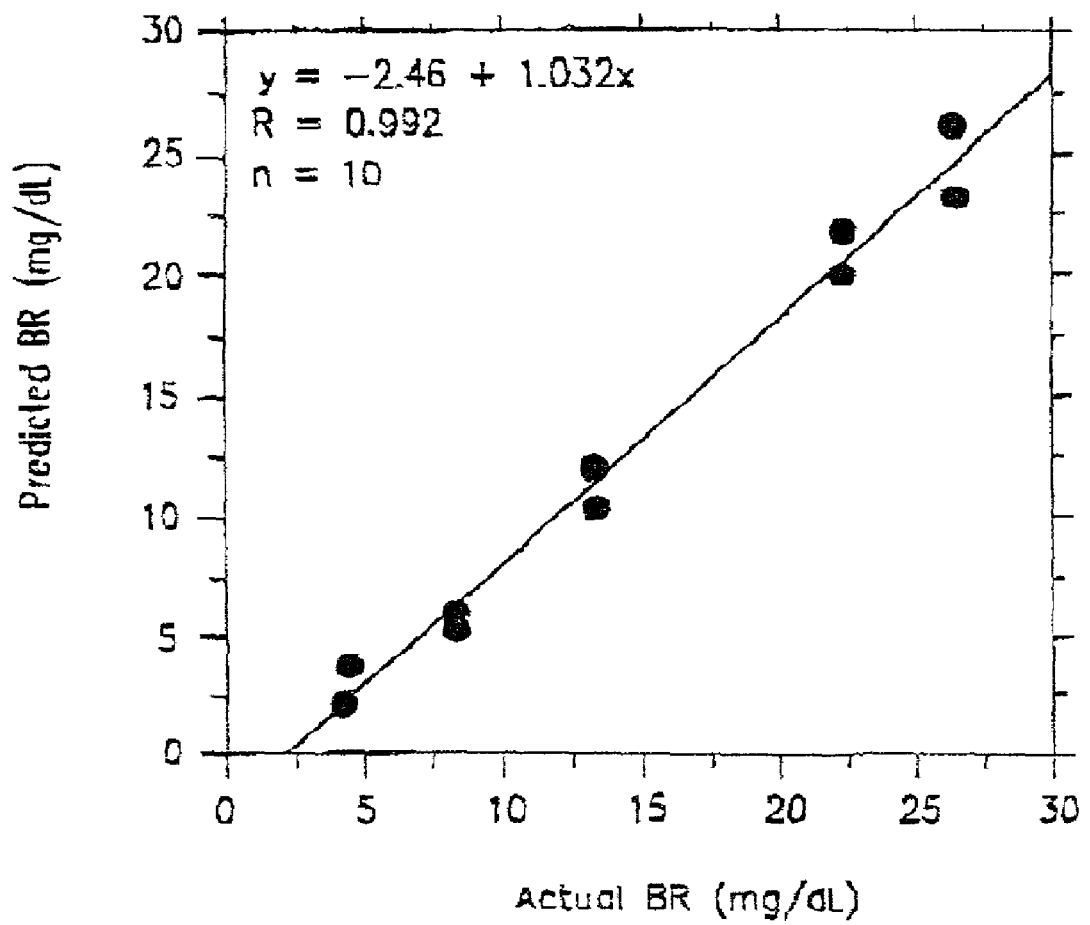
FIG. 15 is a graphic representation of a linear regression fit of data in respect of predicted bilirubin concentration for sample not used in the calibration process, in units of milligrams per deciliter on the abscissa and ordinant axes.
Figure 16:
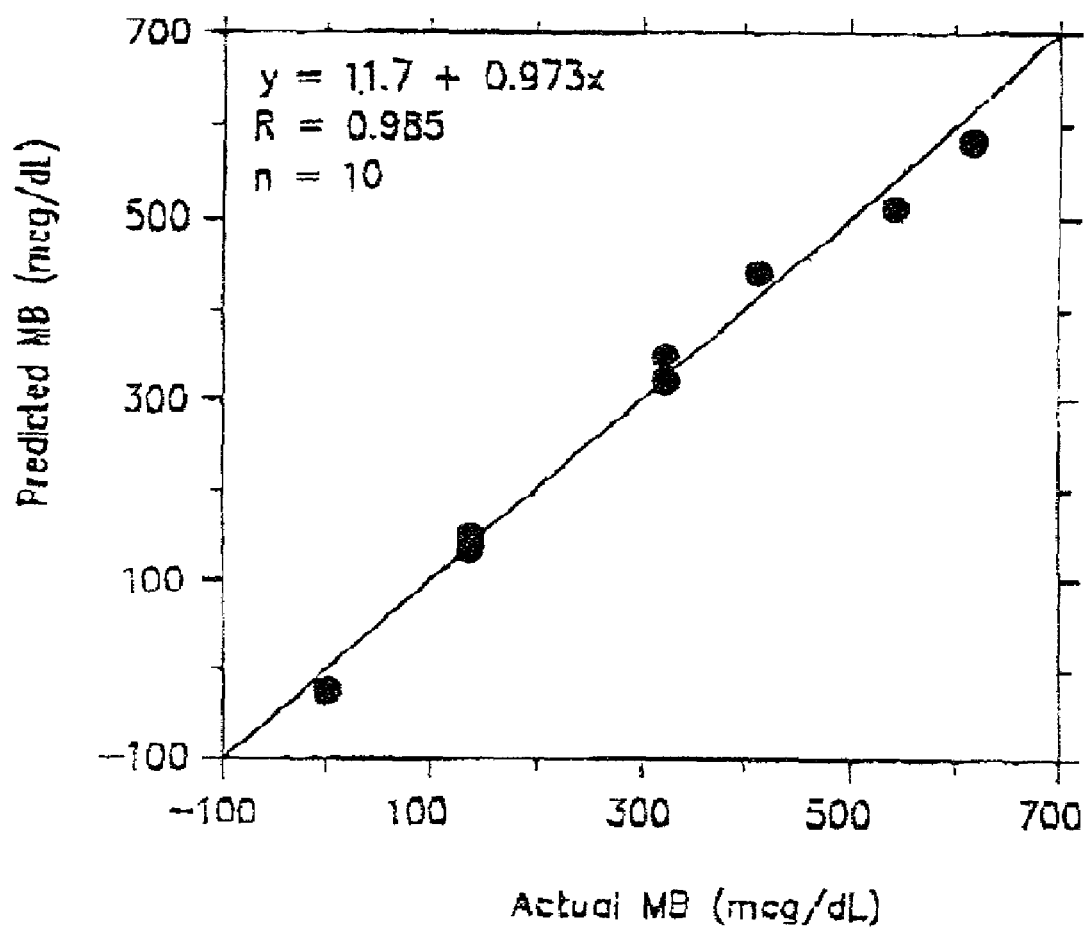
FIG. 16 is a graphic representation of a linear regression fit of data for predicted methylene blue concentration for samples not used in the calibration process, in units of micrograms per deciliter (mcg/dL) on the abscissa and ordinant axes.

FIG. 10 is a graphic representation of the results of a linear regression fit of the data generated from MB calibration. The algorithm which was developed for MB based on this data is as follows:

$$\mu\text{g/dL } MB = 5603.5(677 \text{ nm}) + 26721.43(953 \text{ nm}) + 449.2$$

where the numbers in front of the parentheses on the right hand side of the equation are the first derivative of the absorbance measured at the wavelength specified in the parentheses.

FIGS. 11 to 16 are graphic representations of results of linear regression fits for predicted analyte concentrations for all five analytes described above for samples not used in the calibration processes; two were given for IL based on two different calibration algorithms.

The spectrophotometer can also be calibrated for other analytes such as blood substitutes. For example, in order to calibrate the spectrophotometer for CLHb, serum specimens with normal appearance were spiked with 0 to 16.6 g/L CLHb, 0 to 3.2 g/L Hb, 0 to 4.0 g/L IL, 0 to 48.4 mg/dL BR and 0 to 4.0 mg/dL BV as shown in Table 1.

TABLE 1

Preparation of samples for calibration

| Sample # | Actual Hemolink (g/L) | Hb (g/L) | IL (g/L) | BV (mg/dL) | BR mg/dL) | Fitted Hemolink (g/L) |
|---|---|---|---|---|---|---|
| 1 | 4.91 | 0 | 0 | 0 | 0 | 4.95 |
| 2 | 4.91 | 0 | 0 | 0 | 0 | 5.00 |
| 3 | 2.62 | 0 | 0 | 0 | 0 | 2.86 |
| 4 | 2.62 | 0 | 0 | 0 | 0 | 2.88 |
| 5 | 0 | 0 | 0 | 0 | 0 | 0.19 |
| 6 | 0 | 0 | 0 | 0 | 0 | 0.10 |
| 7 | 7.43 | 0 | 0 | 0 | 0 | 6.63 |
| 8 | 7.43 | 0 | 0 | 0 | 0 | 6.62 |
| 9 | 1.33 | 0 | 0 | 0 | 0 | 1.17 |
| 10 | 1.33 | 0 | 0 | 0 | 0 | 1.09 |

TABLE 1-continued

Preparation of samples for calibration

| Sample # | Actual Hemolink (g/L) | Hb (g/L) | IL (g/L) | BV (mg/dL) | BR mg/dL | Fitted Hemolink (g/L) |
|---|---|---|---|---|---|---|
| 11 | 5.89 | 0 | 0 | 0 | 0 | 5.42 |
| 12 | 5.89 | 0 | 0 | 0 | 0 | 5.39 |
| 13 | 4.17 | 2.36 | 0 | 0 | 0 | 4.51 |
| 14 | 4.17 | 2.36 | 0 | 0 | 0 | 4.52 |
| 15 | 7.36 | 0.77 | 0 | 0 | 0 | 6.36 |
| 16 | 7.36 | 0.77 | 0 | 0 | 0 | 6.54 |
| 17 | 6.58 | 1.16 | 0 | 0 | 0 | 6.06 |
| 18 | 6.58 | 1.16 | 0 | 0 | 0 | 6.06 |
| 19 | 4.21 | 1.59 | 0 | 0 | 0 | 4.51 |
| 20 | 4.21 | 1.59 | 0 | 0 | 0 | 4.41 |
| 21 | 1.72 | 2.03 | 0 | 0 | 0 | 1.93 |
| 22 | 1.72 | 2.03 | 0 | 0 | 0 | 1.92 |
| 23 | 3.33 | 3.15 | 0 | 0 | 0 | 3.99 |
| 24 | 3.33 | 3.15 | 0 | 0 | 0 | 3.92 |
| 25 | 3.3 | 0 | 2.29 | 0 | 0 | 2.83 |
| 26 | 3.3 | 0 | 2.29 | 0 | 0 | 2.71 |
| 27 | 14.75 | 0 | 1.39 | 0 | 0 | 14.90 |
| 28 | 5.81 | 0 | 2.74 | 0 | 48.39 | 6.01 |
| 29 | 5.81 | 0 | 2.74 | 0 | 48.39 | 5.95 |
| 30 | 11.25 | 0 | 3.98 | 0 | 23.44 | 11.05 |
| 31 | 11.25 | 0 | 3.98 | 0 | 23.44 | 10.86 |
| 32 | 8.37 | 0 | 1.98 | 1.55 | 38.76 | 8.46 |
| 33 | 8.37 | 0 | 1.98 | 1.55 | 38.76 | 8.52 |
| 34 | 4.5 | 0 | 2.83 | 0.83 | 33.33 | 5.05 |
| 35 | 4.5 | 0 | 2.83 | 0.83 | 33.33 | 4.91 |
| 36 | 16.62 | 0 | 0 | 1.54 | 7.69 | 16.34 |
| 37 | 16.62 | 0 | 0 | 1.54 | 7.69 | 16.53 |
| 38 | 12.66 | 0 | 0 | 2.34 | 15.63 | 12.79 |
| 39 | 12.66 | 0 | 0 | 2.34 | 15.63 | 12.95 |
| 40 | 7.63 | 0 | 0 | 3.39 | 0 | 8.31 |
| 41 | 7.63 | 0 | 0 | 3.39 | 0 | 8.17 |
| 42 | 10.16 | 0 | 0 | 4.03 | 0 | 9.73 |
| 43 | 10.16 | 0 | 0 | 4.03 | 0 | 9.52 |
| 44 | 9.03 | 0 | 1.84 | 0 | 0 | 9.58 |
| 45 | 10.28 | 0 | 2.07 | 0 | 24.19 | 11.34 |
| 46 | 8.53 | 0 | 3.36 | 0 | 35.91 | 8.5 |
| 47 | 9.81 | 0 | 2.98 | 0.78 | 31.1 | 10.39 |
| 48 | 6.44 | 0 | 2.41 | 1.19 | 36.05 | 5.93 |
| 49 | 1.75 | 0 | 0 | 0 | 0 | 1.86 |
| 50 | 1.75 | 0 | 0 | 0 | 0 | 1.84 |

No significant intercorrelation among the analytes was allowed. The specimens were run once immediately after preparation, and then repeated using different polypropylene pipette disposable tips. Hb was prepared by replacing the normal plasma (by appearance) with water and lysing the erythrocytes through three freeze-thaw cycles. The Hb content of the supernatant of the lysate was measured on an Abbott Cell Dyn.™ The spectra were stored on diskettes. The analyses on a sample set was performed by a statistical computer program and an algorithm was developed for CLHb. Similar calibration sets comprising a blood substitute, for example, CLHb in buffer, and optionally with other compounds or analytes, may be used to generate a calibration algorithm for the blood substitute, such as CHLb. However, it is to be understood that any blood substitute may be used for the preparation of a calibration algorithm as required, using the methods described herein.

A similar method of calibration can be used for a blood bag as described above for the measurement of Hb, and similar results are obtained when the sample is measured within a blood bag. Furthermore, the blood sample may be selected from a range of blood samples including serum, plasma, whole blood, or a buffered solution comprising an analyte, for example, a blood substitute.

An independent sample set was set aside for validation (referred to in the graphical representations as prediction) of the calibration equation, and is shown in Table 2.

TABLE 2

Validation sample set

| Sample # | Actual Hemolink (g/L) | Hb (g/L) | IL (g/L) | BV (mg/dL) | BR (mg/dL) | Predicted Hemolink (g/L) |
|---|---|---|---|---|---|---|
| 1 | 0.85 | 0 | 0 | 0 | 0 | 1.03 |
| 2 | 0.85 | 0 | 0 | 0 | 0 | 1.03 |
| 3 | 3.41 | 0 | 0 | 0 | 0 | 3.73 |
| 4 | 3.41 | 0 | 0 | 0 | 0 | 3.56 |
| 5 | 6.52 | 0 | 0 | 0 | 0 | 5.92 |
| 6 | 6.52 | 0 | 0 | 0 | 0 | 5.89 |
| 7 | 0.87 | 2.05 | 0 | 0 | 0 | 1.09 |
| 8 | 0.87 | 2.05 | 0 | 0 | 0 | 1.13 |
| 9 | 5.83 | 0.79 | 0 | 0 | 0 | 5.54 |
| 10 | 5.83 | 0.79 | 0 | 0 | 0 | 5.45 |
| 11 | 2.5 | 3.94 | 0 | 0 | 0 | 3.77 |
| 12 | 2.5 | 3.94 | 0 | 0 | 0 | 3.50 |
| 13 | 1.31 | 1.24 | 0 | 0 | 0 | 1.28 |
| 14 | 1.31 | 1.24 | 0 | 0 | 0 | 1.34 |
| 15 | 14.75 | 0 | 1.39 | 0 | 0 | 15.24 |
| 16 | 10.56 | 0 | 1.42 | 1.19 | 20.51 | 11.36 |
| 17 | 14.64 | 0 | 0 | 1.94 | 11.66 | 16.36 |
| 18 | 10.14 | 0 | 0 | 2.87 | 7.81 | 10.50 |
| 19 | 8.89 | 0 | 0 | 3.71 | 0 | 8.42 |
| 20 | 6.73 | 0 | 1.15 | 2.02 | 0 | 5.85 |
| 21 | 1.65 | 0 | 1.15 | 0 | 0 | 0.59 |
| 22 | 7.38 | 0 | 0.7 | 0 | 0 | 7.02 |
| 23 | 2.9 | 0 | 1.37 | 0 | 24.19 | 2.67 |
| 24 | 5.63 | 0 | 1.99 | 0 | 11.72 | 4.51 |
| 25 | 4.19 | 0 | 0.99 | 0.78 | 19.38 | 4.04 |
| 26 | 2.25 | 0 | 1.42 | 0.42 | 16.67 | 1.94 |
| 27 | 8.31 | 0 | 0 | 0.77 | 3.85 | 7.78 |
| 28 | 6.33 | 0 | 0 | 1.17 | 7.81 | 6.23 |
| 29 | 3.81 | 0 | 0 | 1.69 | 0 | 3.58 |
| 30 | 5.08 | 0 | 0 | 2.02 | 0 | 4.72 |

Figure 17:
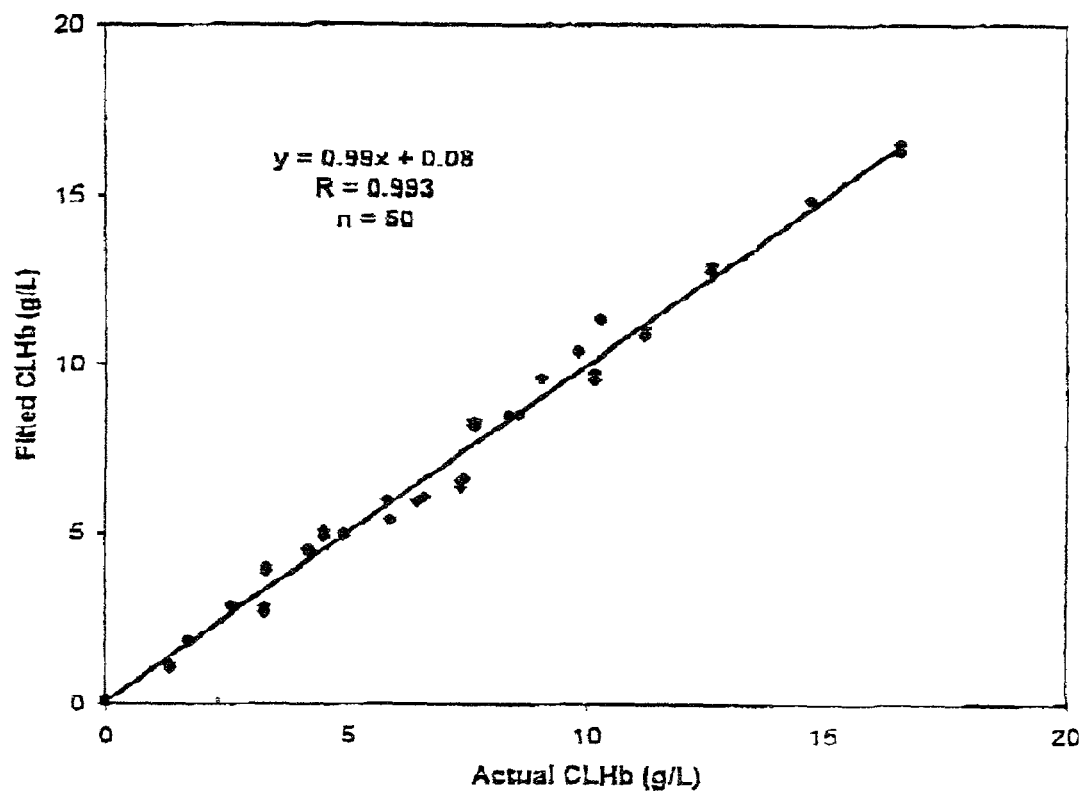
FIG. 17 is a graphic representation of a linear regression fit of the data generated from the CLHb calibration.

FIG. 17 is a graphic representation of a linear regression fit of the data generated from the CLHb calibration. The algorithm which was developed for Hb based on this data is as follows:

$$\text{g/L CLHb} = 23.97(541\ nm) - 76.01(558\ nm) + 130.84(600\ nm) - 113.61(616\ nm) + 0.30$$

where the numbers in front of the parentheses on the right hand side of the equation are the first derivative of the absorbance measured at the wavelength specified in the parentheses.

Figure 18:
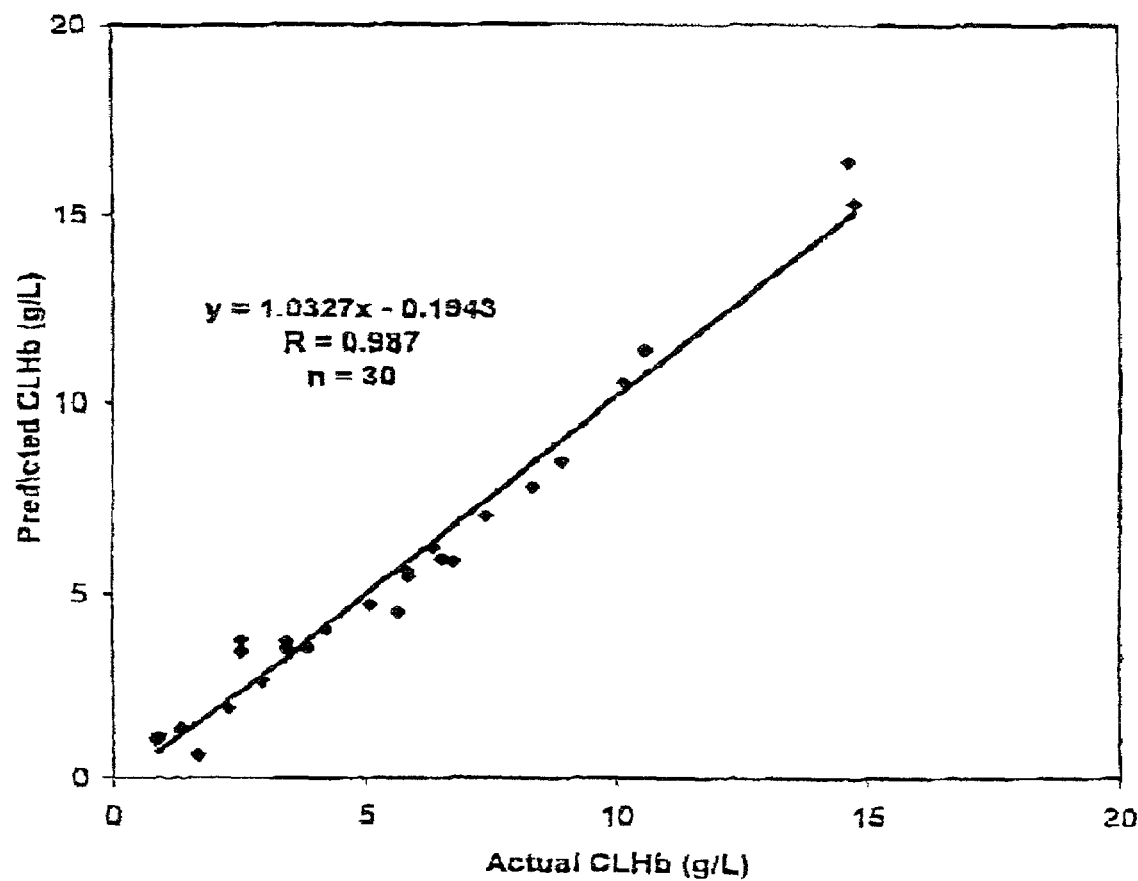
FIG. 18 provides a graphic representation of the results of linear regression fit for predicted CLHb concentration, for samples not used in the calibration processes.

FIG. 18 provides a graphic representation of the results of linear regression fit for predicted CLHb concentration, for samples not used in the calibration processes.

Figure 19:
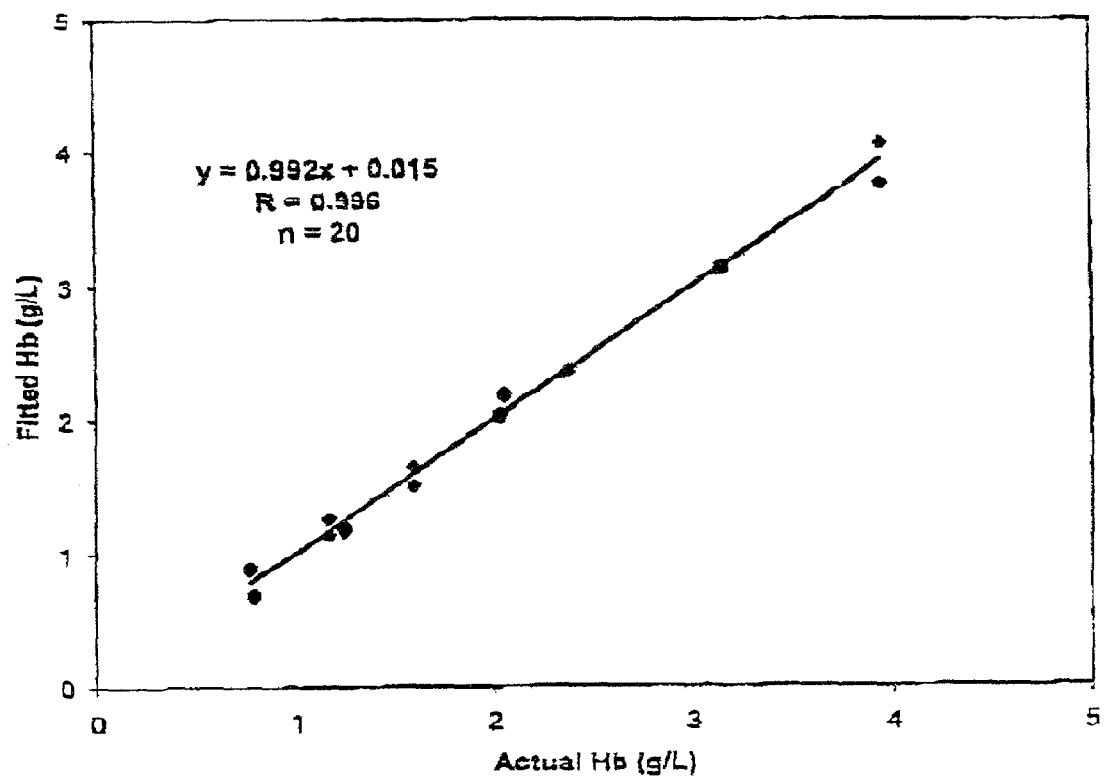
FIG. 19 provides a representation of the results of a linear regression fit of data generated from true Hb calibration in the presence of cross-linked Hb and other analytes (IL, BR, BV).

FIG. 19 provides a graphic representation of the results of a linear regression fit of the data generated from the true Hb calibration with the presence of cross-linked Hb and other analytes (IL, BR, BV). Table 3 provides the individual data points obtained when performing this calibration.

TABLE 3

Calibration data for Hb and CLHb

| CLHb (g/L) | Actual Hb (g/L) | Fitted Hb (g/L) |
|---|---|---|
| 4.17 | 2.36 | 2.35 |
| 4.17 | 2.36 | 2.34 |
| 7.36 | 0.77 | 0.89 |
| 7.36 | 0.77 | 0.87 |
| 6.58 | 1.16 | 1.25 |
| 6.58 | 1.16 | 1.13 |

TABLE 3-continued

Calibration data for Hb and CLHb

| CLHb (g/L) | Actual Hb (g/L) | Fitted Hb (g/L) |
|---|---|---|
| 4.21 | 1.59 | 1.51 |
| 4.21 | 1.59 | 1.64 |
| 0.87 | 2.05 | 2.18 |
| 0.87 | 2.05 | 2.16 |
| 5.83 | 0.79 | 0.67 |
| 5.83 | 0.79 | 0.70 |
| 2.50 | 3.94 | 3.76 |
| 2.50 | 3.94 | 4.05 |
| 1.31 | 1.24 | 1.19 |
| 1.31 | 1.24 | 1.17 |
| 1.72 | 2.03 | 2.01 |
| 1.72 | 2.03 | 2.04 |
| 3.33 | 3.15 | 3.11 |
| 3.33 | 3.15 | 3.15 |

The algorithm which was developed as a result of the calibration above, is as follows:

g/L $\quad Hb=-0.72+30.72(558 \text{ nm})-17.40(570 \text{ nm})+171.14(730 \text{ nm})$ where the numbers in front of the parentheses on the right hand side of the equation are the first derivative of the absorbance measured at the wavelength specified in the parentheses.

As will be readily understood by those skilled in the art, several algorithms can be developed for each analytes using different groups of wavelengths with the resultant prediction performance by the different algorithms for the same analytes being similar.

While the invention has been particularly shown and described with reference to certain embodiments, it will be understood by those skilled in the art that various other changes in form and detail may be made without departing from the spirit and scope of the invention.

We claim:

1. A method for determining a concentration of one, or more than one analyte in a sample contained in a blood bag or in a tubing in fluid communication with said blood bag, using an instrument comprising one, or more than one calibration algorithm for said one, or more than one analyte, said method comprising:
   a) irradiating said sample in said tubing, or said blood bag, using a radiation source of about 475 nm to about 2,700 nm;
   b) measuring an absorbance of said sample; and
   c) calculating a concentration of said one, or more than one analyte using said absorbance and said one, or more than one calibration algorithm.

2. The method of claim 1, wherein said step of calculating (step c)) comprises determining values of first derivatives of two, or more than two portions of a spectrum generated from said step of measuring (step b), and incorporating said first derivatives into said one, or more than one calibration algorithm to provide said concentration.

3. The method of claim 1 wherein said blood bag, or said tubing is translucent and contains writing on its surface and irradiation is transmitted through said writing, said blood bag or said tubing, and said sample contained in said blood bag or said tubing.

4. The method of claim 1 wherein said step of irradiating (step a)) includes reflecting radiation from a reflective surface placed behind said blood bag or said tubing.

5. The method of claim 2 wherein in said step of measuring (step b)), light leakages are compensated for by measuring dark current for both sample and reference measurements.

6. The method of claim 2, wherein said one, or more than one analyte is selected from the group consisting of haemoglobin, bilirubin, biliverdin, equivalent intralipid, methylene blue and cross-linked haemoglobin.

7. The method of claim 1, wherein said one, or more than one analyte is selected from the group consisting of haemoglobin, bilirubin, biliverdin, equivalent intralipid, methylene blue, and cross-linked haemoglobin.

8. A method for determining a concentration of one, or more than one of haemoglobin, bilirubin, biliverdin, equivalent intralipid, methylene blue and cross-linked haemoglobinin in a sample contained in a blood bag or in a tubing in fluid communication with said blood bag, using an instrument comprising one, or more than one calibration algorithm for each of said haemoglobin, bilirubin, biliverdin, equivalent intralipid, methylene blue and cross-linked haemoglobin, said method comprising:
   a) irradiating said sample in said tubing or said blood bag using a radiation source of about 475 nm to about 2,700 nm;
   b) measuring an absorbance of said sample, and
   c) calculating a concentration for one, or more than one of said haemoglobin, bilirubin, biliverdin, equivalent intralipid, methylene blue and cross-linked haemoglobin by determining values of first derivatives of two, or more than two portions of a spectrum generated from said step of measuring (step b), and incorporating said first derivatives into said one, or more than one calibration algorithm to provide said concentration.

* * * * *